United States Patent
Caillard

(10) Patent No.: US 11,737,987 B2
(45) Date of Patent: Aug. 29, 2023

(54) ORAL DELIVERY SYSTEMS BASED ON IN SITU FORMING PROTEIN/POLYSACCHARIDE COACERVATES

(71) Applicant: 9286-3620 Québec Inc., Levis (CA)

(72) Inventor: Romain Caillard, Levis (CA)

(73) Assignee: 9286-3620 QUEBEC INC., Levis (CA)

( * ) Notice: Subject to any disclaimer, the term of this patent is extended or adjusted under 35 U.S.C. 154(b) by 0 days.

(21) Appl. No.: 17/604,282

(22) PCT Filed: Dec. 16, 2020

(86) PCT No.: PCT/CA2020/051726
§ 371 (c)(1),
(2) Date: Oct. 15, 2021

(87) PCT Pub. No.: WO2021/119810
PCT Pub. Date: Jun. 24, 2021

(65) Prior Publication Data
US 2022/0087941 A1 Mar. 24, 2022

Related U.S. Application Data

(60) Provisional application No. 62/949,130, filed on Dec. 17, 2019.

(51) Int. Cl.
*A61K 9/20* (2006.01)
*A23P 10/30* (2016.01)
*A61K 9/48* (2006.01)
*A61K 45/06* (2006.01)

(52) U.S. Cl.
CPC ............ *A61K 9/2063* (2013.01); *A23P 10/30* (2016.08); *A61K 9/205* (2013.01); *A61K 9/4866* (2013.01); *A61K 45/06* (2013.01)

(58) Field of Classification Search
CPC .... A61K 9/205; A61K 9/2063; A61K 9/4866; A61K 45/06; A61K 31/045; A61K 31/12; A61K 31/198; A61K 31/375; A61K 31/4045; A61K 35/747; A61K 36/064; A61K 36/534; A61K 36/8962; A61K 31/405; A61K 31/4415; A61K 31/522; A61K 31/706; A61K 36/9068; A61K 38/168; A61K 47/36; A61K 47/42; A61K 2300/00; A61K 9/0053; A23P 10/30; A23P 10/28
See application file for complete search history.

(56) References Cited

U.S. PATENT DOCUMENTS

| | | |
|---|---|---|
| 3,069,327 A | 12/1962 | Eldridge et al. |
| 3,312,594 A | 4/1967 | Gilman |
| 3,558,768 A | 1/1971 | Klippel |
| 4,267,275 A | 5/1981 | Muller |
| 4,451,446 A | 5/1984 | Vandevelde et al. |
| 4,614,794 A | 9/1986 | Easton et al. |
| 4,753,796 A | 6/1988 | Moreno et al. |
| 6,224,905 B1 | 5/2001 | Lawrence et al. |
| 6,632,451 B2 | 10/2003 | Penhasi et al. |
| 8,137,728 B2 | 3/2012 | McClements et al. |
| 8,722,062 B2 | 5/2014 | Ryall |
| 8,728,556 B2 | 5/2014 | Schmitt et al. |
| 8,795,724 B2 | 8/2014 | Caillard et al. |
| 8,900,630 B2 | 12/2014 | Yan et al. |
| 8,936,786 B2 | 1/2015 | Vol et al. |
| 9,526,692 B2 | 12/2016 | Rehage |
| 2007/0275061 A1 | 11/2007 | Jo et al. |
| 2008/0254119 A1* | 10/2008 | Dai ....................... A23L 29/035 514/23 |
| 2011/0083681 A1 | 4/2011 | Sengupta et al. |
| 2015/0050245 A1 | 2/2015 | Herman et al. |
| 2016/0361261 A1* | 12/2016 | Carpanzano ......... A61K 9/1652 |
| 2018/0213823 A1 | 8/2018 | Asai et al. |
| 2019/0076535 A1 | 3/2019 | Held et al. |
| 2019/0328023 A1 | 10/2019 | Parekh et al. |

FOREIGN PATENT DOCUMENTS

| | | |
|---|---|---|
| WO | 2003026687 A1 | 4/2003 |
| WO | 2003106014 A1 | 12/2003 |
| WO | 2009028764 A1 | 3/2009 |
| WO | 2011124876 A2 | 10/2011 |
| WO | 2018224191 A1 | 12/2018 |

OTHER PUBLICATIONS

Ertan. J Microencapsulation. 1997; 14(3): 379-388. (Year: 1997).*
Abdullah et al. Physics Interntional. 2010; 1(1): 16-21. (Year: 2010).*
USP 35: United States Pharmacopeia and the National Formulary (USP 35-NF 30). Rockville (MD): The United States Pharmacopeial Convention; 2012. (Year: 2012).*
Anonymous. Basicmedical Key [online]; 2016; downloaded from <URL https://basicmedicalkey.com/powder-properties/ > on Jul. 26, 2022; 5 pages. (Year: 2016).*
Al-Hashemi, H.M.B., and Al-Amoudi, O.S.B., "A review on the angle of repose of granular materials", Powder Technology 330:397-417 (2018).
Blocher, W.C., and Perry, S.L., "Complex coacervate-based materials for biomedicine", WIREs Nanomed Nanobiotechnol 2016. doi: 10.1002/wnan.1442, 28 pages.

(Continued)

*Primary Examiner* — David Browe

(57) ABSTRACT

An oral delivery system based on in situ forming protein/polysaccharide coacervates is described herein. The system comprises an uncoacervated, dry homogenous mixture comprising a protein powder, a polysaccharide powder, and an active ingredient dispersed therein, wherein the polysaccharide powder has a Carr compressibility index greater than 25% to enable the protein and polysaccharide powders to form a protein/polysaccharide complex coacervate in situ upon immersion of the oral delivery system in a gastric fluid, thereby conferring gastric protection and/or modified release to the active ingredient.

22 Claims, 24 Drawing Sheets

(56) References Cited

OTHER PUBLICATIONS

Boschini, F., et al., "Linking flowability and granulometry of lactose powders", International Journal of Pharmaceutics 494:312-320 (2015).
Bouyer, E., et al., "Proteins, polysaccharides, and their complexes used as stabilizers for emulsions: Alternatives to synthetic surfactants in the pharmaceutical field?" International Journal of Pharmaceutics 436:359-378 (2012).
Calvo, P., et al., "Novel Hydrophilic Chitosan-Polyethylene Oxide Nanoparticles as Protein Carriers" Applied Polymer 63(1): 125-132 (1997).
Comert, F., et al., "Coacervation and Precipitation in Polysaccharide-protein Systems", Soft Matter DOI: 10.1039/C6SM00044D (2016) 25 pages.
De Kruif, C.G., and Tuinier, R., "Polysaccharide protein interactions", Food Hydrocolloids 15:555-563 (2001).
De Kruif, C.G., et al., "Complex coacervation of proteins and anionic polysaccharides", Current Opinion in Colloid & Interface Science 9:240-249 (2004).
Devi, N., et al., "Encapsulation of active ingredients in polysaccharide-protein complex coacervates, Advances in Colloid and Interface Science"239:136-145 (2017).
Dickinson, Eric, "Stability and rheological implications of electrostatic milk protein-polysaccharide interactions" Food Science & Technology 9:347-354 (1998).
Doublier, J-L., et al., "Protein-polysaccharide interactions", Current Opinion in Colloid & Interface Science 5:202-214 (2000).
Elmoneim, A., et al., "Study of the physical properties of kafirin during the fabrication of tablets for pharmaceutical applications", Journal of Cereal Science 50:159-165 (2009).
Elzoghby, A.O., et al., "Casein-based formulations as promising controlled release drug delivery systems", Journal of Controlled Release 153:206-216 (2011).
Georget, D.M.R., et al., "A study on maize proteins as a potential new tablet excipient", European Journal of Pharmaceutics and Biopharmaceutics 69:718-726 (2008).
Gilbert, V., et al., "Characterization and evaluation of whey protein-based biofilms as substrates for in vitro cell cultures", Biomaterials 26:7451-7480 (2005).
Imeson, A.P., et al., "On the Nature of the Interaction Between some Anionic Polysaccharides and Proteins", J. Sci. Fd Agric. 28:661-668 (1977).
Johnson, N.R., and Wang, Y., "Coacervate delivery systems for proteins and small molecule drugs", Expert Opin Drug Deliv 11(12): 1829-1832 (2014).
Jones, O.G., and McClements, D.J., "Recent progress in biopolymer nanoparticle and microparticle formation by heat-treating electrostatic protein-polysaccharide complexes", Advances in Colloid and interface Science 167:49-62 (2011).
Kaibara, K., et al., "pH-Induced Coacervation in Complexes of Bovine Serum Albumin and Cationic Polyelectrolytes", Biomacromolecules 1:100-107 (2000).
Katayama, H., et al., "Application of Fibroin in Controlled Release Tablets Containing Theophylline", Biol Pharm Bull 23 (10):1229-1234 (2000).
Klein, Sandra, "The Use of Biorelevant Dissolution Media to Forecast the in Vivo Performance of a Drug", The AAPS Journal 12(3):397-406 (2010).
Ledward, D.A., "Protein-Polysaccharide Interactions", J. Inst. Can. Sci. Technol. Aliment 12(1):A16 (1979) Abstract.
Li, Yunqi and Huang, Qingrong, "Protein-polysaccharide complexes for effective delivery of bioactive functional food ingredients", Chapter 14 in Nanotechnology and Functional Foods: Effective Delivery of Bioactive Ingredients, First Edition. Sabliov, CM, Chen, H, and Yada, R.Y., Eds. (2015).
Liu, S., et al., "Intermolecular Interactions during Complex Coacervation of Pea Protein Isolate and Gum Arabic", J. Agric. Food Chem. 58:552-556 (2010).

Qui, Y. and Lee, P.I., "Rational Design of Oral Modified-Release Drug Delivery Systems", Chapter 19 in Developing Solid Oral Dosage Forms (2017). 36 pages.
Sah, B.N.P., et al., "Modulation of bovine whey protein digestion in gastrointestinal tract: A comprehensive review", International Dairy Journal 62:10-18 (2016).
Schmitt, C., and Turgeon, S.L., "Protein/polysaccharide complexes and coacervates in food systems", Advances in Colloid and Interface Science 167:63-70 (2011).
Schmitt, C., et al., "Structure and Technofunctional Properties of Protein-Polysaccharide Complexes: A Review", Critical Reviews in Food Science and Nutrition 38(8):689-753 (1998).
Schmitt, Christophe, "Etude de la coacervation complexe entre la beta-lactoglobuline et la gomme d'acacia en solution aqueuse". Sciences agricoles. Institut National Polytechnique de Lorraine, Francais (2000). [Eng Abstract—Thesis].
Syrbe, A., et al., "Polymer Science Concepts in Dairy Systems—An Overview of Milk Protein and Food Hydrocolloid Interaction", Int. Dairy Journal 8: 179-193 (1998).
Timilsena, Y.P., et al., "Complex coacervation: Principles, mechanisms and applications in microencapsulation", International Journal of Biological Macromolecules DOI:10.1016/j.ijbiomac.2018.10.144 (2018).
Tiwari, S.B., and Rajabi-Siahboomi, A.R., "Applications of Complementary Polymers in HPMC Hydrophilic Extended Release Matrices", Drug Delivery Technology 9(7):20-27 (2009).
Tolstoguzov, Vladimir B., "Protein-Polysaccharide Interactions—Chapter 6" in Food Proteins and Their Applications, Damodarar, Srinivasan, 1st Ed. (1997) 28 pages. Abstract.
Turgeon, S.L, et al., "Protein-polysaccharide complexes and coacervates", Current Opinion in Colloid Interface Science 12:166-178 (1007).
Weinbreck, Fanny, "Whey protein/gum Arabic coacervates: structure and dynamics", Thesis Utrecht University, The Netherlands 2004, 208 pages.
Zambrano, V., et al., "Insights about stabilization of sulforaphane through microencapsulation", Heliyon 5:e02951 (2019).
Zayas, J.F., "Solubility of Proteins" Chapter 1 in Functionality of Proteins in Food, Springer-Verlag Berlin Heidelberg (1997).
Zerfaβ, Christian, "Examining Coacervate Formation at Protein-Polysaccharide Interfaces", News Medical Life Sciences [online] [retrieved on Jun. 12, 2019]. Retrieved from Internet URL: https://www.news-medical.net/life-sciences/Examining-Coacervate-Formation-at-Protein . . . .
International Search Report International application No. PCT/CA2020/051726, dated Mar. 19, 2021, 4 pages.
Jonat, Stéphane et al. "Investigation of the glidant properties of compacted colloidal silicon dioxide by angle of repose and X-ray photoelectron spectroscopy." European journal of pharmaceutics and biopharmaceutics vol. 63,3 (2006).
Blanco, David et al. "Effect of colloidal silicon dioxide and moisture on powder flow properties: Predicting in-process performance using image-based analysis." International journal of pharmaceutics vol. 597 (2021).
Legoix, Léonard et al., "Characterizing powders in order to determine their flow behavior in a mixer: From small scale observations to macroscopic in-mixer rheology for powders of various flowabilities." Powder Technology, vol. 322, 2017, pp. 314-331.
Devi, Nirmala; Kakati, Dilip Kumar., "Smart porous microparticles based on gelatin/sodium alginate polyelectrolyte complex" Journal of Food Engineering, vol. 117, Issue 2, Jul. 2013, pp. 193-204.
Ghosal et al., "Agglomeration of a model food powder: Effect of maltodextrin and gum Arabic dispersions on flow behavior and compacted mass"Journal of Food Engineering 96 (2010) 222-228.
Mao, L., Pan, Q., Yuan, F., Gao, Y., Formation of soy protein isolate-carrageenan complex coacervates for improved viability of Bifidobacterium longum during pasteurization and in vitro digestion, Food Chemistry (2018).
European Search Report and Written Opinion for the European Application No. EP20901042, dated Nov. 11, 2022, 10 pages.

* cited by examiner

ORAL DELIVERY SYSTEMS BASED ON IN SITU FORMING PROTEIN/POLYSACCHARIDE COACERVATES

CROSS REFERENCE TO RELATED APPLICATION

This application is a national stage filing under 35 U.S. § 371 of Intl. Appln. No. PCT/CA2020/051726, filed Dec. 16, 2020, which claims the benefit of provisional application U.S. Ser. No. 62/949,130, filed Dec. 17, 2019, each of which is incorporated herein by reference in its entirety.

The present description relates to oral delivery systems for active ingredients. More particularly, described herein are versatile solid oral delivery systems comprising protein/polysaccharide powder mixtures that form protein/polysaccharide complex coacervates in situ upon exposure to gastric environments, thereby providing gastric protection and/or modified-release to the active ingredients.

BACKGROUND

Modified-release oral forms are specific products formulated so that the release of an active ingredient is modulated. In this way, specific objectives that cannot be attained with conventional dosage forms can be reached. These products present several advantages including possible therapeutic benefits, improved efficacy, reduced adverse effects, optimized performance, or increased convenience and patient compliance. While various modified-release oral delivery systems currently exist, many of these systems utilize synthetic compounds and/or polymers that a growing body of consumers (and therefore companies) are seeking to avoid, particularly for active ingredients that are to be taken regularly. Furthermore, many modified-release oral delivery systems in current use require complex, multistep processes for their manufacture, such as applying multiple coatings or layers to an oral dosage form. Thus, alternative oral delivery systems employing more natural ingredients and simplified manufacturing steps are highly desirable.

SUMMARY

In one aspect, described herein is an oral delivery system comprising a dry homogenous mixture comprising a protein powder and a polysaccharide powder mixture, and an active ingredient dispersed therein, the protein and polysaccharide powder mixture forming a protein/polysaccharide complex coacervate in situ upon immersion of the oral delivery system in a gastric fluid, thereby conferring gastric protection and/or modified release to the active ingredient, wherein varying the ratio of protein powder to polysaccharide powder in the oral delivery system varies the level of gastric protection and/or rate of release of the active ingredient.

In a further aspect, described herein is a process for preparing a solid oral dosage form, the process comprising dispersing an active ingredient in a dry homogenous mixture comprising a protein powder and a polysaccharide powder, and formulating the resulting mixture into a solid oral dosage form, the polysaccharide powder having powder flow characteristics enabling interaction with the protein powder such that immersion of the solid oral dosage form in a gastric fluid results in formation of a protein/polysaccharide complex coacervate in situ, thereby conferring gastric protection and/or modified-release to the active ingredient.

In a further aspect, described herein is a method for producing a protein/polysaccharide complex coacervate in situ that confers gastric protection and/or modified-release to an active ingredient dispersed therein, the method comprising providing the active ingredient formulated in an oral delivery system described herein, or formulated in an oral dosage form produced be a process described herein, and orally administering the oral delivery system or the oral dosage form to a subject, wherein the protein and polysaccharide powder mixture forms the protein/polysaccharide complex coacervate in situ upon immersion of the oral delivery system in the subject's gastric fluid.

In a further aspect, described herein is a method for treating a disease or condition ameliorated by administration to a subject of an active ingredient which would benefit from gastric protection and/or modified-release, the method comprising providing the active ingredient formulated in an oral delivery system described herein, or formulated in an oral dosage form produced be a process described herein, and orally administering the oral delivery system or the oral dosage form to a subject, wherein the protein and polysaccharide powder mixture forms a protein/polysaccharide complex coacervate in situ upon immersion of the oral delivery system in the subject's gastric fluid.

In embodiments, polysaccharide powders suitable for use in the oral delivery systems described herein possess particular powder flow characteristics associated with powders that are increasing cohesive (or decreasingly flowable), as characterized by minimum thresholds for parameters such as angle of repose ($\alpha$), dynamic cohesive index, Hausner ratio, and/or compressibility index (Carr index).

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or process/method steps.

DETAILED DESCRIPTION

Figure 1:
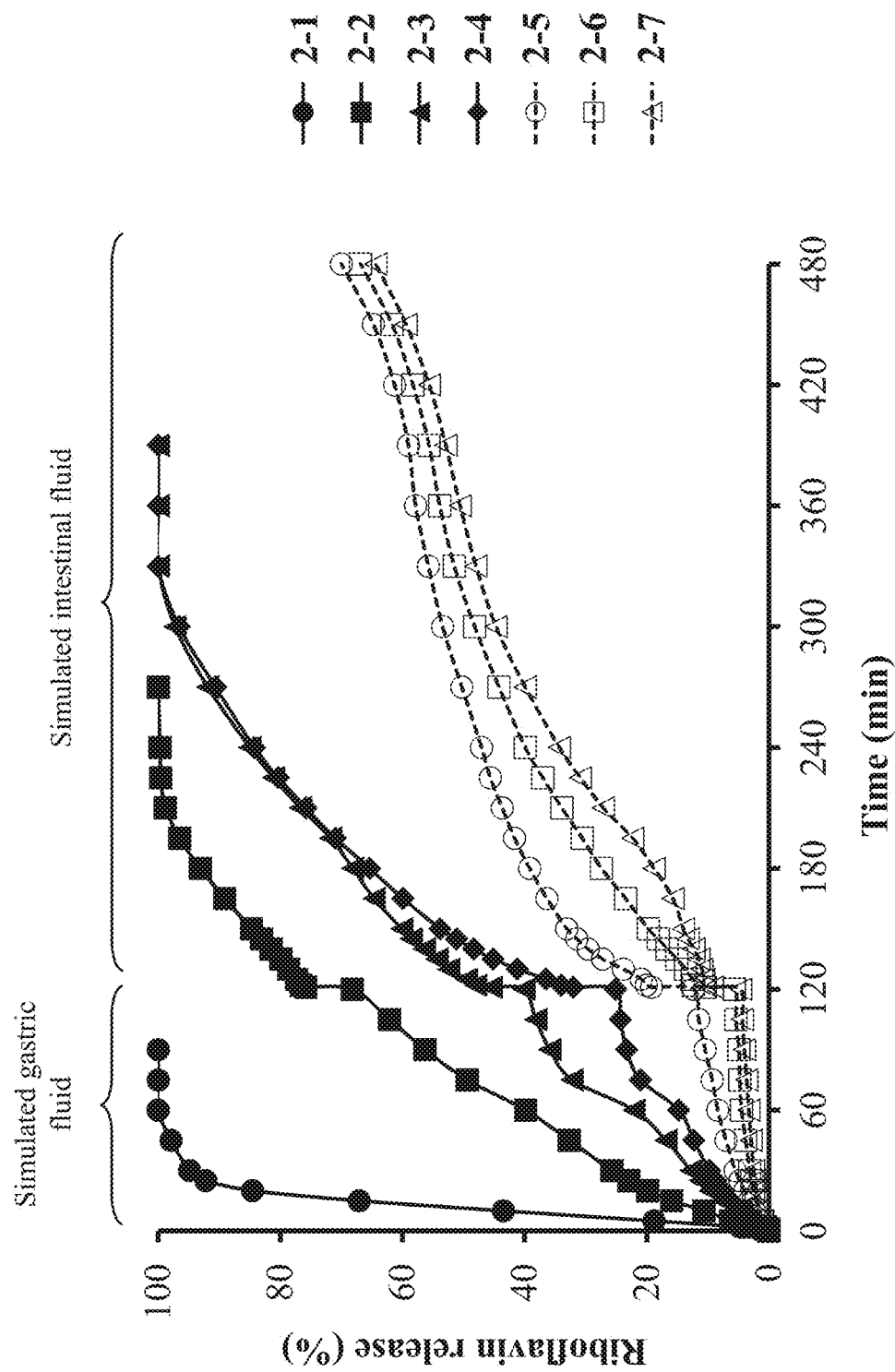
FIG. 1: In vitro release profiles of formulations 2-1 to 2-7.

Described herein is a versatile oral delivery system useful for conferring gastric protection and/or modified-release to a variety of active ingredients formulated therein. In general, the oral delivery system utilizes dry particulate biopolymer ingredients that are blended together and formulated with an active ingredient in a solid oral dosage form such that immersion of the solid oral dosage form in a gastric fluid results in formation of a complex biopolymer-based coacervate in situ. The degree of gastric protection and/or modified-release conferred to the active ingredient is governed by structural properties of the complex coacervate formed in situ, which is in turn controllable by the nature and ratio of the particulate/powdered ingredients employed in the oral delivery system. Furthermore, the ability of the oral delivery system described herein to be based on natural and/or naturally-derived biopolymers (e.g., food biopolymers) provide commercial advantages in terms of regulatory approval and/or addressing the growing consumer demand for such products.

A wide variety of natural ingredients were screened herein with the goal of developing a versatile natural ingredient-based oral delivery system suitable for providing gastric protection and/or modified-release to a variety of active ingredients. Empirical dissolution testing involving monitoring release of the active ingredients after sequential exposure to simulated gastric fluid and simulated intestinal fluid revealed that certain mixtures of proteins and polysaccharides powders were able to provide gastric protection and slower release to active ingredients formulated therewith. For example, it was observed that a mixture of whey protein powder and a kappa-carrageenan powder (i.e., linear sulfated polysaccharides extracted from red edible seaweeds) in a tablet or capsule formulation provided increased protection of different active ingredients from simulated gastric fluid, as well as slower active ingredient release over time (Example 1). Further experiments were performed to characterize the structure, mechanism, and reproducibility of whey protein and kappa-carrageenan powder mixtures for use in oral delivery systems. More specifically, the effect of protein/polysaccharide powder mixture ratios and native/denatured proteins on active ingredient release properties in tablet formulations were explored in Example 2, and the structural properties of the protein/polysaccharide coacervate-like complexes formed in situ upon immersion in gastric fluid were explored in Example 3. The versatility of the oral delivery systems described herein for use in capsule formulations is shown in Example 4.

Interestingly, while the nature/source of the protein powder employed in the oral delivery system described herein was relatively flexible (i.e., proteins from different sources and/or suppliers could be substituted without significantly affecting gastric protection and/or modified-release performance), employing the same type of polysaccharides powder from different suppliers yielded wildly unpredictable results. For example, it was observed that kappa-carrageenan powders and xanthan gum powders from different suppliers yielded opposite results in terms of tablet erosion testing (Example 5 and Table 6). Furthermore, without subjecting the oral formulations to empirical dissolution testing, it was not possible to reliably predict beforehand (e.g., based on supplier-provided product specification sheets) which polysaccharides from which suppliers would successfully form stable, complex coacervates in situ. These unpredictable results led to extensive efforts to identify objective and measurable parameters that could reliably predict polysaccharide powders suitable for the in situ coacervate-forming oral delivery systems described herein. In particular, these efforts resulted in a set of measurable/calculatable parameters relating to the powder flow characteristics of the polysaccharide powder (i.e., dynamic cohesive index, angle of repose, compressibility index (Carr index), and/or Hausner ratio) that could be used to reliably predict its suitability for the in situ coacervate-forming oral delivery systems described herein (Table 7). Furthermore, a polysaccharide powder associated with poor gastric protection in oral delivery systems described herein (i.e., 100% disintegration in 12 minutes in simulated gastric fluid) was subjected to a conditioning step to increase its cohesiveness in Example 6. The conditioned polysaccharide powder not only had a more favorable parameter profile in terms of dynamic cohesive index, angle of repose, compressibility index (Carr index), and/or Hausner ratio, but also exhibited a remarkable increase in gastric protection (i.e., only 1% disintegration in simulated gastric fluid) in an oral delivery system (Table 9). The parameters were subsequently validated for use in the oral delivery systems described herein in the context of a variety of different protein powders, polysaccharide powders, active ingredients, and additives (Examples 7-22). Accordingly, various aspects and embodiments relating to the technology described herein are discussed below.

In some aspects, the oral delivery system described herein comprises (or consists essentially of) an active ingredient dispersed in a dry, relatively homogenous powder mixture, which are then formulated into a solid oral dosage form. The homogenous powder mixture comprises a mixture of a protein powder and a polysaccharide powder, and may further comprise one or more additives (e.g., pharmaceutically acceptable excipients) depending on the particular solid oral dosage form (e.g., tablet or capsule). The particles of proteins and polysaccharides in the powder mixture of the oral delivery system interact such that immersion of the oral delivery system in a gastric or simulated gastric fluid results in the formation of protein/polysaccharide complex coacervates in situ, thereby conferring gastric protection and/or modified release to an active ingredient dispersed therein. In some embodiments, the particles of proteins and polysaccharides in the powder mixture of the oral delivery system may interact to form an interactive powder mixture.

As used herein, the expression "oral delivery system" refers not only to a vendible product but also a versatile platform that can be used to formulate a variety of active ingredients for gastric protection and/or modified-release, which is based on the in situ-forming protein/polysaccharide complex coacervates described herein. The platform is scalable in the sense that the degree of gastric protection and/or modified release is controllable by varying the properties and/or ratio of the protein and polysaccharide powders employed. The oral delivery system can be utilized to prepare specific oral dosage forms (e.g., tablets or capsules) that are compatible for use therewith. For greater clarity, the oral delivery systems referred to herein exclude oral dosage forms that may happen to contain polysaccharides and proteins amongst other ingredients, wherein the polysaccharides and proteins are not intended to form complex coacervates in situ upon immersion in gastric fluid, or the polysaccharides and proteins are not the principal agents responsible for the gastric protection or modified-release characteristics of the oral dosage form.

As used herein, the expression "consisting essentially of" in the context of oral delivery systems described herein excludes oral dosage forms that may contain polysaccharides and proteins amongst other ingredients, but in which the polysaccharides and proteins do not form complex coacervates in situ upon immersion in gastric fluid and in which the level of gastric protection and/or modified-release conferred to the active ingredient (if any) is not governed or controlled by the strength of the complex coacervate formed.

As used herein, "coacervate" or "complex coacervate" refers to the binding, assembling or clustering of proteins and polysaccharides in the presence of a liquid. As reported in the scientific literature, stable coacervation generally occurs when two oppositely charged biopolymers are mixed in a liquid, usually at a pH between the pKa of the polysaccharides and below the isoelectric point of the proteins. Coacervation does not occur when proteins and polysaccharides are mixed in their powder forms in the absence of liquid.

In some embodiments, the oral delivery system described herein is adaptable/scalable to the desired level of gastric protection and/or rate of release of the active ingredient. For example, in some embodiments, varying the ratio (e.g., weight ratio) of polysaccharide powder to protein powder in the homogenous powder mixture of the oral delivery system varies the level of gastric protection and/or rate of release of the active ingredient. In some embodiments, increasing the ratio (e.g., weight ratio) of polysaccharide powder to protein powder in the oral delivery system increases the level of gastric protection conferred to the active ingredient, and/or decreases the rate of release of the active ingredient (e.g., in gastric or simulated gastric fluid) by the oral delivery system—e.g., see Example 2 and FIG. 1. In some embodiments, the weight ratio of polysaccharide powder to protein power in the oral delivery system is 1:20 to 1:1, 1:15 to 1:1.5, 1:10 to 1:2, 1:9.5 to 1:2.5, 1:9 to 1:3, or 1:8.5 to 1:3.5, 1:8 to 1:4, 1:7.5 to 1:4.5, or 1:7 to 1:5. In some embodiments, the weight ratio is from any one of [1:20, 1:19, 1:18, 1:17, 1:16, 1:15, 1:14 1:13, 1:12, 1:11, 1:10, 1:9, 1:8, 1:7, 1:6, or 1:5] to any one of [1:4, 1:3, 1:2, or 1:1].

In some embodiments, the level of gastric protection and/or modified-release conferred to an active ingredient may be controlled by the amount of protein/polysaccharide powder mixture present in the oral delivery system. In some embodiments, the oral delivery system may comprise about 5% to 50%, 10% to 45%, 15% to 40%, or 20% to 35% w/w of the protein/polysaccharide powder mixture.

In some embodiments, the protein and polysaccharide powder mixture forms a protein/polysaccharide complex coacervate in situ upon immersion of the oral delivery system in a solution of pH below the pKa of the polysaccharide (e.g., gastric or simulated gastric fluid), which is able to remain intact upon subsequent incubation at a pH above the isoelectric point of the protein (e.g., intestinal or simulated intestinal fluid). This is an atypical property of coacervates in general, since the scientific literature consistently reports that stable protein/polysaccharide coacervates form in a pH range of between the pKa of the polysaccharides and the isoelectric point of the protein material (Syrbe et al., 1998; Tolstoguzov, 1997). In some embodiments, the protein and polysaccharide powder mixture forms a protein/polysaccharide complex coacervate in situ upon immersion of the oral delivery system in a simulated gastric fluid (SGF) consisting of a 37% v/v solution of diluted HCl at pH 1.0, containing 2 g/L of NaCl and 0.1 g/L of pepsin.

In some embodiments, the level of gastric protection and/or modified-release conferred to the active ingredient is governed by the structural properties (i.e., strength) of the protein/polysaccharide complex coacervate formed in situ upon immersion in a gastric fluid. In some embodiments, the active ingredient's rate of release is inversely proportional to the strength of the protein/polysaccharide complex coacervate formed in situ upon immersion of the oral delivery system in the gastric fluid. In some embodiments, the protein/polysaccharide complex coacervate formed in situ upon immersion of the oral delivery system in the SGF is characterized by the presence of intramolecular beta-sheets, alpha-helices, and/or unordered structures (e.g., as measured by Fourier transform infrared (FTIR) spectroscopy; such as by the methods described in Example 3).

In some embodiments, the oral delivery system described herein preferably comprises a dry, relatively homogenous powder mixture comprising a mixture of a protein powder and a polysaccharide powder, wherein the polysaccharide powder has powder flow characteristics enabling the formation of a protein/polysaccharide complex coacervate in situ upon immersion in a gastric fluid having sufficient strength to impart gastric protection and/or modified release to an active ingredient formulated therewith. In some embodiments, the polysaccharide powder may be characterized by its flowability, texture, and/or cohesiveness as measured by its angle of repose (α), dynamic cohesive index, Hausner ratio, and/or compressibility index (Carr index), according to the methods recommended in USP <1174>. In some embodiments, protein/polysaccharide coacervates of increasing strength form with the use of polysaccharide powders that are increasing cohesive (or decreasingly flowable), as measured by the angle of repose, dynamic cohesive index, Hausner ratio, and/or compressibility index (Carr index). In some embodiments, coacervation of increased strength may occur when the polysaccharide and protein possess oppositely charged groups.

"Angle of repose" generally refers to the static or dynamic measurement of the steepest angle of a material from the horizontal plane on which the material can be heaped without collapsing (Beakawi Al-Hashemi, H. et al., 2018). The angle of repose can be measured for example by the "tilting box method", "fixed-funnel method", "revolving cylinder/drum method", or a GranuHeap™ (GranuTools™, Awans, Belgium). The maximum angle of repose is 90 degrees. Lower angles of repose (e.g., values below 35 degrees) correspond to more free-flowing materials. Higher angles of repose (e.g., over 35 degrees) indicate more cohesive (non-flowing) powders. Angle of repose can also be measured by forming a cone of powder on a stable base, as recommended in USP <1174>.

In some embodiments, the polysaccharide powders employed in the oral delivery systems described herein have an angle of repose associated with powders having fair (36-40 degrees), passable (41-45 degrees), poor (46-55 degrees), very poor (56-65 degrees), or very, very poor (56-65 degrees) flowability per the classification by Carr (Carr, R. L., 1965) reproduced in USP <1174>, such as when measured by the method recommended by USP <1174>. Briefly, the recommended method comprises forming a symmetrical cone of powder by allowing the powder to pass through a funnel onto a fixed base with a retaining lip to retain a layer of powder on the base; varying the height of the funnel to maintain a distance of approximately 2-4 cm from the top of the powder pile as it is being formed; and determining the angle of repose by measuring the height of the cone of powder and calculating the angle of repose from the following equation:

$$\tan(\alpha) = \frac{\text{height}}{0.5 \text{ base}}.$$

In some embodiments, the polysaccharide powders employed in the oral delivery systems described herein have an angle of repose greater than about 28, 29, 30, 31, 32, 33, 34, 35, 36, 37, 38, 39, 40, 41, 42, 43, 44, 45, 46, 47, 48, 49, 49, 50, 51, 52, 53, 54, 55, 56, 57, 58, 59, 60, 61, 62, 63, 64, or 65 degrees, as measured according to method recommended in USP <1174>.

In some embodiments, the polysaccharide powders employed in the oral delivery systems described herein have a dynamic cohesive index above a threshold value. "Dynamic cohesive index", as used herein refers to the qualitative evaluation of the surface slope fluctuations of a material. The dynamic cohesive index can also be measured by instruments such as rheometers like the GranuDrum™ (GranuTools™, Awans, Belgium). Higher dynamic cohesive index values (e.g., between 30 and 60), refer to materials that are more cohesive. Lower dynamic cohesive index values (e.g., between 0 and 30), refer to materials that are less cohesive. In some embodiments, the polysaccharide powder employed in the oral delivery systems described herein have a dynamic cohesive index greater than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, the polysaccharide powders employed in the oral delivery systems described herein have a compressibility index (Carr index) above a threshold value. "Carr index" or "compressibility index", as used herein, refers to the compressibility of a powder or material, as described in USP <1174> and measured by the formula:

$$\text{Compressibility Index} = 100 \times \left(\frac{\rho_{tapped} - \rho_{bulk}}{\rho_{tapped}}\right),$$

wherein $\rho_{tapped}$ and $\rho_{bulk}$ refer to the tapped density and bulk density of the powder, respectively. Higher compressibility indexes (e.g., index over 15%), indicate a powder that is weakly flowable (more cohesive). Lower compressibility indexes (e.g., index below 15%), indicate to a powder that is more flowable (less cohesive). In some embodiments, the polysaccharide powders employed in the oral delivery systems described herein have a compressibility index associated with powders having fair (16-20%), passable (21-25%), poor (26-31%), very poor (32-37%), or very, very poor (greater than 38%) flowability, as set forth in USP <1174>. In some aspects, the polysaccharide powders employed in the oral delivery systems described herein have a compressibility index greater than about 15, 16, 17, 18, 19, 20, 21, 22, 23, 24, 25, 26, 27, 28, 29, 30, 31, 32, 33, 34, 35, 36, 37, or 38%, for example as measured by the method described above.

In some embodiments, the polysaccharide powders employed in the oral delivery systems described herein have a Hausner ratio above a threshold value. "Hausner ratio", as used herein, refers to the flowability of a powder as described in USP <1174> and measured by the formula:

$$\text{Hausner Ratio} = \left(\frac{\rho_{tapped}}{\rho_{bulk}}\right),$$

wherein $\rho_{tapped}$ and $\rho_{bulk}$ refer to the tapped density and bulk density of the powder, respectively. Higher Hausner ratios (e.g., over 1.18), indicate powders that are more weakly flowable (more cohesive). Lower Hausner ratios (e.g., below 1.18), indicate to powders that are more flowable (less cohesive). In some embodiments, the polysaccharide powders employed in the oral delivery systems described herein have a Hausner ratio associated with powders having fair (1.19-1.25), passable (21-25%), poor (26-31%), very poor (32-37%), or very, very poor (greater than 38%) flowability, as set forth in USP <1174>. In some embodiments, the polysaccharide powders employed in the oral delivery systems described herein have a Hausner ratio greater than about 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, or 1.6, for example as measured by the method described above.

In some embodiments, the polysaccharide powders described herein may be conditioned to have sufficient cohesiveness prior to formulation in an oral delivery system described herein, such as having one or more of an angle of repose ($\alpha$), dynamic cohesive index, Hausner ratio, and/or compressibility index (Carr index), as described herein. In some embodiments, the conditioning may comprise any treatment that increases cohesiveness and/or reduces flowability of the polysaccharide powder. For example, the conditioning may comprise one or more of dissolving, lyophilizing, drying, grinding, and/or sifting the polysaccharide powder through a suitably-sized mesh, to increase the floury texture of the powder, as well as its cohesiveness.

In some embodiments, the oral delivery systems described herein may inhibit the release of the active ingredient into the gastric fluid, and extend, prolong, sustain, control, slow or delay the release of the active ingredient into the intestinal fluid. As used herein, the term "modified-release" refers to the property of the solid oral dosage form in extending, delaying, slowing, or controlling the release of the active ingredient. In some embodiments, modified-release occurs after formation of the protein/polysaccharide complex coacervates upon immersion of the oral delivery system in a gastric fluid.

In some embodiments, the oral delivery systems described herein may be a delayed-release oral delivery system, an extended-release oral delivery system, an oral delivery system providing increased gastric protection to the active ingredient upon oral administration, as compared to administration of an unformulated active ingredient; or any combination thereof. In some embodiments, the delayed release oral delivery system may delay the time required for 50% of the active ingredient to be released by at least 30, 60, 90, 120, 150, 180, 210, or 240 minutes, as compared to a corresponding oral delivery system lacking the polysaccharide powder. In some embodiments, the extended-release oral delivery system may result in release of the active ingredient over a period of at least 3, 4, 5, 6, 7, 8, 9, 10, 11, 12, 13, 14, 15, 16, 17, or 18 hours. In some embodiments, the oral delivery system may provide increased gastric protection to the active ingredient as compared to administration of an unformulated active ingredient. In some embodiments, the aforementioned modified-release and/or gastric protection values may refer to those obtained upon dissolution testing comprising immersion of the oral delivery system at 37° C. in SGF for two hours followed by immersion in simulated intestinal fluid (SIF), wherein the SGF consists of a 37% v/v diluted HCl solution, pH 1.0, containing 2 g/L of NaCl and 0.1 g/L of pepsin, and the SIF consists of a 50 mM $NaH_2PO_4$ or $KH_2PO_4$ buffer solution at pH 6.9, containing 0.5 g/L of pancreatin.

In some embodiments, the protein powders employed in the oral delivery systems described herein may comprise or consist of: natural proteins; food-grade and/or pharmaceutical-grade proteins; native proteins; denatured proteins (e.g., thermally denatured proteins); chemically unmodified proteins; chemically modified proteins (e.g., succinylated proteins); plant proteins (e.g., hemp, sacha inchi); animal proteins; dairy proteins (e.g., whey protein); legume proteins (e.g., pea or soy protein); fruit protein (e.g., coconut); cereal proteins (e.g., rice); or any mixture thereof.

In some embodiments, the polysaccharide powders employed in the oral delivery systems described herein may comprise or consist of: natural polysaccharides; food-grade and/or pharmaceutical-grade polysaccharides; chemically unmodified polysaccharides; chemically modified polysaccharides;

plant polysaccharides; animal polysaccharides; polysaccharides containing negatively charged/acidic groups (anionic polysaccharides); carrageenan (e.g., kappa-carrageenan); xanthan gum; alginate; pectin powder; agar, gellan, guar gum, carboxymethylcellulose, locust bean gum, mannan, glucomannan, hyaluronan, tamarind gum, psyllium seed gum, tara gum, acacia gum, arabic gum, ghatti gum, tragacanth gum, karaya gum, cassia gum, rhamsan gum, welan gum, macrophomopsis gum, curdlan, pullulan, fucoidan, or any mixture thereof.<

As used herein, "active ingredient" refers to any molecule, substance or microorganism that is therapeutically or biologically active. In some embodiments, active ingredients described herein may comprise or consists of a dietary supplement, a drug (e.g., caffeine), a probiotic (e.g., probiotic bacteria or yeast, such as *Saccharomyces boulardii* or *Pediococcus acidilactici*), a prebiotic, a vitamin (e.g., vitamin B2/riboflavin or B6), an amino acid (e.g., 5-Hydroxytryptophan[5-HTP]), a food or plant extract (e.g., peppermint extract, rice extract, rice hull extract, or curcumin), or an herbal supplement (e.g., goldenrod extract and ginger). In some embodiments, the active ingredient may be in powder or granular form.

In some embodiments, oral delivery systems described herein may further comprise one or more nutraceutically or pharmaceutically acceptable excipients and/or additives (e.g., a filler, a binder, a lubricant, a flow agent). Such excipients and/or additives vary depending on the type of oral dosage form being formulated (e.g., tablet or capsule). In some embodiments, the excipients and/or additives may comprise microcrystalline cellulose, magnesium stearate, stearic acid, dibasic calcium phosphate, calcium carbonate, dextrose, and/or silicon dioxide.

In some embodiments, the oral delivery systems described herein may comprise a homogenous admixture of the protein powder, polysaccharide powder, and an active ingredient, which are compressed to form a tablet. In some embodiments, the homogenous admixture comprises one or more pharmaceutically acceptable excipients or additives (e.g., as described herein), which could be filler agents, binders, lubricants, and/or flowing agents.

In some embodiments, the oral delivery systems described herein may comprise a homogenous admixture of the protein powder, polysaccharide powder, and an active ingredient, filled in a capsule (e.g., gel- or cellulose-based). In some embodiments, the capsule may be a macrocapsule. In some embodiments, the capsule may be a microcapsule.

In some embodiments, the oral delivery system described herein preferably does not comprise an enteric coating.

In some aspects, described herein is a process for preparing a solid oral dosage form, the process comprising dispersing an active ingredient in a dry homogenous mixture comprising a protein powder and a polysaccharide powder, and formulating the resulting mixture into a solid oral dosage form. In some embodiments, the polysaccharide powder has powder flow characteristics enabling interaction with the protein powder such that immersion of the solid oral dosage form in a gastric fluid results in formation of a protein/polysaccharide complex coacervate in situ, thereby conferring gastric protection and/or modified-release to the active ingredient.

In some embodiments, the processes described herein employ polysaccharide powders having one or more of the powder flow characteristics as defined herein, e.g., relating to dynamic cohesive index, angle of repose, compressibility index (Carr index), and/or Hausner ratio.

In some embodiments, the processes described herein are for preparing an oral delivery system as described herein.

In some aspects, described herein is the oral delivery system as described herein, or the oral dosage form produced by the process as described herein, for use in therapy. In some embodiments, the therapy is a disease or condition ameliorated by oral administration of an active ingredient formulated in the oral delivery system or oral dosage form described herein.

In some aspects, described herein is a method for producing a protein/polysaccharide complex coacervate in situ that confers gastric protection and/or modified-release to an active ingredient dispersed therein. The method comprises providing the active ingredient formulated in the oral delivery system as described herein, or formulated in the oral dosage form produced be a process as described herein, and orally administering the oral delivery system or the oral dosage form to a subject, wherein the protein and polysaccharide powder mixture forms the protein/polysaccharide complex coacervate in situ upon immersion of the oral delivery system in the subject's gastric fluid.

In some aspects, described herein is a method for treating a disease or condition ameliorated by administration to a subject of an active ingredient which would benefit from gastric protection and/or modified-release. The method comprises providing the active ingredient formulated in the oral delivery system as described herein, or formulated in the oral dosage form produced be a process as described herein, and orally administering the oral delivery system or the oral dosage form to the subject, wherein the protein and polysaccharide powder mixture forms a protein/polysaccharide complex coacervate in situ upon immersion of the oral delivery system in the subject's gastric fluid.

Items

1. An oral delivery system comprising (or consisting essentially of) a dry homogenous mixture comprising a protein powder and a polysaccharide powder mixture, and an active ingredient dispersed therein, the protein and polysaccharide powder mixture forming a protein/polysaccharide complex coacervate in situ upon immersion of the oral delivery system in a gastric fluid, thereby conferring gastric protection and/or modified release to the active ingredient, wherein varying the ratio of protein powder to polysaccharide powder in the oral delivery system varies the level of gastric protection and/or rate of release of the active ingredient.
2. The oral delivery system of item 1, wherein the polysaccharide powder has, or is conditioned to have, one or more of the following powder flow characteristics: (a) an angle of repose ($\alpha$) greater than about 28, 29, 30, 31, 32, 33, 34, 35, 36, 37, 38, 39, 40, 41, 42, 43, 44, 45, 46, 47, 48, 49, 49, 50, 51, 52, 53, 54, 55, 56, 57, 58, 59, 60, 61, 62, 63, 64, or 65 degrees; (b) a dynamic cohesive index greater than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50; (c) a compressibility index (Carr index) greater than about 15, 16, 17, 18, 19, 20, 21, 22, 23, 24, 25, 26, 27, 28, 29, 30, 31, 32, 33, 34, 35, 36, 37, or 38%; (d) a Hausner ratio greater than about 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, or 1.6; or (e) any combination of (a) to (d).
3. The oral delivery system of item 2, wherein the polysaccharide powder has, or is conditioned to have, all the powder flow characteristics as defined in (a), (b), (c) and (d).
4. The oral delivery system of any one of items 1 to 3, wherein the protein and polysaccharide powder mixture forms a protein/polysaccharide complex coacervate in situ upon immersion of the oral delivery system in a solution of pH below the pKa of the polysaccharide.
5. The oral delivery system of any one of items 1 to 4, wherein: (a) increasing the ratio of polysaccharide powder to protein power in the oral delivery system increases the level of gastric protection and/or decreases the rate of release to the active ingredient; (b) the weight ratio of polysaccharide powder to protein power in the oral delivery system is 1:20 to 1:1, 1:15 to 1:1.5, 1:10 to 1:2, 1:9.5 to 1:2.5, 1:9 to 1:3, or 1:8.5 to 1:3.5, 1:8 to 1:4, 1:7.5 to 1:4.5, or 1:7 to 1:5; (c) the oral delivery system comprises about 5% to 50%, 10% to 45%, 15% to 40%, or 20% to 35% w/w of the protein and polysaccharide mixture; or (d) any combination thereof.
6. The oral delivery system of any one of items 1 to 5, wherein: (a) the protein and polysaccharide powder mixture forms a protein/polysaccharide complex coacervate in situ upon immersion of the oral delivery system in a simulated gastric fluid (SGF) consisting of a 37% v/v solution of diluted HCl at pH 1.0, containing 2 g/L of NaCl and 0.1 g/L of pepsin; (b) the active ingredient's rate of release is inversely proportional to the strength of the protein/polysaccharide complex coacervate formed in situ upon immersion of the oral delivery system in the gastric fluid; (c) the protein/polysaccharide complex coacervate formed in situ upon immersion of the oral delivery system in the SGF is characterized by the presence of intramolecular beta-sheets, alpha-helices, and/or unordered structures (e.g., as measured by Fourier transform infrared (FTIR) spectroscopy); or (d) any combination thereof.
7. The oral delivery system of any one of items 1 to 6, which is: (i) a delayed-release oral delivery system; (ii) an extended-release oral delivery system; (iii) an oral delivery system providing increased gastric protection to the active ingredient upon oral administration, as compared to administration of an unformulated active ingredient; or (iv) any combination thereof.
8. The oral delivery system of item 7, wherein: (i) the delayed release oral delivery system delays the time required for 50% of the active ingredient to be released by at least 30, 60, 90, 120, 150, 180, 210, or 240 minutes, as compared to a corresponding oral delivery system lacking the polysaccharide powder; (ii) the extended-release oral delivery system results in release of the active ingredient over a period of at least 3, 4, 5, 6, 7, 8, 9, 10, 11, 12, 13, 14, 15, 16, 17, or 18 hours; and/or (ii) the oral delivery system provides increased gastric protection to the active ingredient as compared to administration of an unformulated active ingredient; upon dissolution testing comprising immersion of the oral delivery system at 37° C. in SGF for two hours followed by immersion in simulated intestinal fluid (SIF), wherein the SGF consists of a 37% v/v diluted HCl solution, pH 1.0, containing 2 g/L of NaCl and 0.1 g/L of pepsin, and the SIF consists of a 50 mM $NaH_2PO_4$ or $KH_2PO_4$ buffer solution at pH 6.9, containing 0.5 g/L of pancreatin.

9. The oral delivery system of any one of items 1 to 8, wherein the protein powder comprises or consists of: natural proteins; food-grade and/or pharmaceutical-grade proteins; native proteins; denatured proteins (e.g., thermally denatured proteins); chemically unmodified proteins; chemically modified proteins (e.g., succinylated proteins); plant proteins (e.g., hemp, sacha inchi); animal proteins; dairy proteins (e.g., whey protein); legume proteins (e.g., pea or soy protein); fruit protein (e.g., coconut); cereal proteins (e.g., rice); or any mixture thereof.

10. The oral delivery system of any one of items 1 to 9, wherein the polysaccharide powder comprises or consists of: natural polysaccharides; food-grade and/or pharmaceutical-grade polysaccharides; chemically unmodified polysaccharides; chemically modified polysaccharides; plant polysaccharides; animal polysaccharides; polysaccharides containing negatively charged/acidic groups (anionic polysaccharides); carrageenan (e.g., kappa-carrageenan); xanthan gum; alginate; pectin powder; agar, gellan, guar gum, carboxymethylcellulose, locust bean gum, mannan, glucomannan, hyaluronan, tamarind gum, psyllium seed gum, tara gum, acacia gum, arabic gum, ghatti gum, tragacanth gum, karaya gum, cassia gum, rhamsan gum, welan gum, macrophomopsis gum, curdlan, pullulan, fucoidan, or any mixture thereof.

11. The oral delivery system of any one of items 1 to 10, wherein the active ingredient is a dietary supplement, a drug, a probiotic, a vitamin, an amino acid, a food extract, or an herbal supplement.

12. The oral delivery system of any one of items 1 to 11, further comprising one or more nutraceutically or pharmaceutically acceptable excipients and/or additives (e.g., a filler, a binder, a lubricant, and/or a flow agent).

13. The oral delivery system of item 12, wherein the additive is or comprises microcrystalline cellulose, magnesium stearate, and/or silicon dioxide.

14. The oral delivery system of any one of items 1 to 13, which is a tablet or a capsule.

15. The oral delivery system of any one of items 1 to 14, wherein the oral delivery system does not comprise an enteric coating.

16. A process for preparing a solid oral dosage form, the process comprising dispersing an active ingredient in a dry homogenous mixture comprising a protein powder and a polysaccharide powder, and formulating the resulting mixture into a solid oral dosage form, the polysaccharide powder having powder flow characteristics enabling interaction with the protein powder such that immersion of the solid oral dosage form in a gastric fluid results in formation of a protein/polysaccharide complex coacervate in situ, thereby conferring gastric protection and/or modified-release to the active ingredient.

17. The process of item 16, wherein the polysaccharide powder has one or more of the powder flow characteristics as defined in item 2.

18. The process of item 16 or 17, wherein solid oral dosage form is the oral delivery system as defined in any one of items 1 to 15.

19. The oral delivery system as defined in any one of items 1 to 15, or the oral dosage form produced by the process of any one of items 16 to 18, for use in therapy.

20. A method for producing a protein/polysaccharide complex coacervate in situ that confers gastric protection and/or modified-release to an active ingredient dispersed therein, the method comprising providing the active ingredient formulated in the oral delivery system as defined in any one of items 1 to 15, or formulated in the oral dosage form produced be the process of any one of items 16 to 18, and orally administering the oral delivery system or the oral dosage form to a subject, wherein the protein and polysaccharide powder mixture forms the protein/polysaccharide complex coacervate in situ upon immersion of the oral delivery system in the subject's gastric fluid.

21. A method for treating a disease or condition ameliorated by administration to a subject of an active ingredient which would benefit from gastric protection and/or modified-release, the method comprising providing the active ingredient formulated in the oral delivery system as defined in any one of items 1 to 15, or formulated in the oral dosage form produced be the process of any one of items 16 to 18, and orally administering the oral delivery system or the oral dosage form to a subject, wherein the protein and polysaccharide powder mixture forms a protein/polysaccharide complex coacervate in situ upon immersion of the oral delivery system in the subject's gastric fluid.

EXAMPLES

Example 1

Screening Natural Ingredients for Use in Protein-Based Oral Delivery Systems

With the goal of developing natural ingredient-based modified-release oral delivery systems that are relatively simple to manufacture, extensive screening was performed using a wide variety of natural ingredients to manufacture solid oral dosage forms. Specifically, food-grade natural ingredients from different sources and suppliers, alone and in various combinations, were formulated with different active ingredients—all in their dry forms—as either tablet or capsule oral formulations. The oral formulations were then subjected to dissolution testing involving sequential exposure to simulated gastric fluid and simulated intestinal fluid, followed by monitoring release of the active ingredients over time. Particular emphasis in the screening was placed on natural ingredients that could be used in the context of protein-based oral formulations to achieve a degree of gastric protection and/or slower release of the active ingredient.

Interestingly, the results of the extensive screening efforts revealed that certain mixtures of proteins and polysaccharides powders formulated with various active ingredients were able to provide gastric protection and slower release of the active ingredients in the context of oral formulations. For example, it was observed that a mixture of whey protein powder and a kappa-carrageenan powder (i.e., linear sulfated polysaccharides extracted from red edible seaweeds) in a tablet or capsule formulation was able to provide increased protection of different active ingredients from simulated gastric fluid, as well as slower active ingredient release over time. Further experiments to characterize the structure, mechanism, and reproducibility of whey protein and kappa-carrageenan powder mixtures for use in gastric protecting and/or modified-release oral delivery systems were carried out, as described in the Examples below.

Example 2

Effect of Protein/Polysaccharide Powder Mixture Ratios and Native/Denatured Proteins on Active Ingredient Release Properties in Tablet Formulations

2.1 Tablet Manufacturing

All ingredients in this Example, except for whey proteins, were sourced from the same supplier hereinafter referred to as supplier A. Riboflavin (vitamin B2) was chosen as an active ingredient. Native whey proteins (Agropur Ingredients, Le Sueur, Minn., USA) were thermally denatured for 30 min. at 85° C. Tablets were prepared by direct compression using a TDP-6 single punch press (Yangzhou Nuoya Machinery co. Ltd., Jiangju, China). Powders were weighed and subsequently mixed together in a mortar prior to tabletting. Tablet diameters and thicknesses were respectively 11.2 mm and 6.5 mm. 24 h after manufacture, tablet hardness was measured following the United States Pharmacopeia (USP) <1217>, using a Tablet Hardness Tester YD-1 (Minsheng Pharmaceutical Machinery Ltd., Shangai, China). Hardness was between 7 and 9 kp. Formulations tested in this Example are described in Table 1.

TABLE 1

Tablet formulations tested in Example 2

| | | Native whey proteins | | | Denatured whey proteins | | |
|---|---|---|---|---|---|---|---|
| | FORMULATION (in mg) | 2-1 | 2-2 | 2-3 | 2-4 | 2-5 | 2-6 | 2-7 |
| Proteins | Native whey proteins | 295 | 265 | 235 | 205 | 0 | 0 | 0 |
| | Denatured whey proteins | 0 | 0 | 0 | 0 | 265 | 235 | 205 |
| Polysaccharides | kappa-carrageenan | 0 | 30 | 60 | 90 | 30 | 60 | 90 |
| Active ingredient | Vitamin B2 | 50 | 50 | 50 | 50 | 50 | 50 | 50 |
| Additives | Microcrystalline cellulose (MCC) | 15 | 15 | 15 | 15 | 15 | 15 | 15 |
| | Magnesium stearate | 4 | 4 | 4 | 4 | 4 | 4 | 4 |
| | Silicon dioxide | 1 | 1 | 1 | 1 | 1 | 1 | 1 |

2.2 Tablet Dissolution Testing

In vitro performance of tablets was tested using a dissolution apparatus SR6 Dissolution test station, USP II (Hanson Research Corp., Chatsworth, Calif.). Guidelines described in USP <2040> (Disintegration and dissolution of dietary supplements) were followed.

During experiments, paddle speed was set at 100 rpm and the temperature was maintained at 37° C. Prior to measurements, samples were filtered and background absorbance was subtracted. Release was followed by measuring the concentration of the active ingredient (AI) dissolved in the release medium as a function of time. Absorbance at 440 nm was followed using an UV-Vis spectrophotometer.

Typical dissolution experiments consisted of the immersion of 3 tablets into a simulated gastric fluid (SGF) for 2 h, followed by the immersion of the tablets into a simulated intestinal fluid (SIF), until complete dissolution. No sinkers were used.

SGF consisted of a diluted HCl (37%) solution, pH 1.0, containing 2 g/L of NaCl and 0.1 g/L of pepsin. SIF consisted of a $NaH_2PO_4$ buffer (50 mM), pH 6.9, containing 0.5 g/L of pancreatin. Experiments were repeated at least two times.

2.3 In Vitro Riboflavin Release from Tablet Dissolution Testing

FIG. 1 illustrates the in vitro release profiles obtained from formulations 2-1 to 2-7 (see Table 1). Tablets containing no polysaccharides (formulation 2-1) quickly released the riboflavin: after 45 min, riboflavin was completely released and tablets were dissolved.

Tablets containing both native whey proteins and kappa-carrageenan showed slower release profiles of riboflavin. After 2 h, the percent release was 68%, 41%, and 24% for formulations 2-2, 2-3, and 2-4, respectively. Complete release occurred after 225 min, 330 min, and 330 min for formulations 2-2, 2-3, and 2-4, respectively. These results indicate that the presence of the polysaccharide (kappa-carrageenan) decreased the rate of release of riboflavin. Furthermore, these results suggest that the higher the polysaccharide to protein ratio, the lower the rate of release of the active ingredient.

Replacing the native whey proteins in formulations 2-2, 2-3, and 2-4 with corresponding amounts of denatured whey proteins (i.e., formulations 2-5, 2-6, and 2-7) resulted in an even slower release rate of the active ingredient. Indeed, after 8 hours of experiment, riboflavin release was between 65% and 70% for formulations 2-5 to 2-7 (FIG. 1). Of note, the use of denatured proteins resulted in a particularly slower release of riboflavin during exposure to SGF (0 to 120 min) (FIG. 1).

Example 3

Protein/Polysaccharide Powder Mixtures form Coacervates In Situ

In order to investigate the structures and physiochemical properties of the tablet formulations of Example 2 following exposure to SGF and SIF, at least two types of tests were performed: Strength testing in the presence or absence of chaotropic agents; and Fourier transform infrared (FTIR) spectroscopy.

3.1 Strength Measurements in the Presence or Absence of Chaotropic Agents

Tablets prepared as described in Example 2.1 were immersed in either 50 mL of SGF for 2 h, or in 50 mL of SGF for 2 h followed by immersion in SIF for 2 h, as described in Example 2.2. Although all of formulations 2-2 to 2-7 formed what appeared to be coacervate-like complexes during the course of the incubations, only formulations 2-5, 2-6, and 2-7 were sufficiently strong to be physically manipulated and thus were selected for further study.

Figure 2:
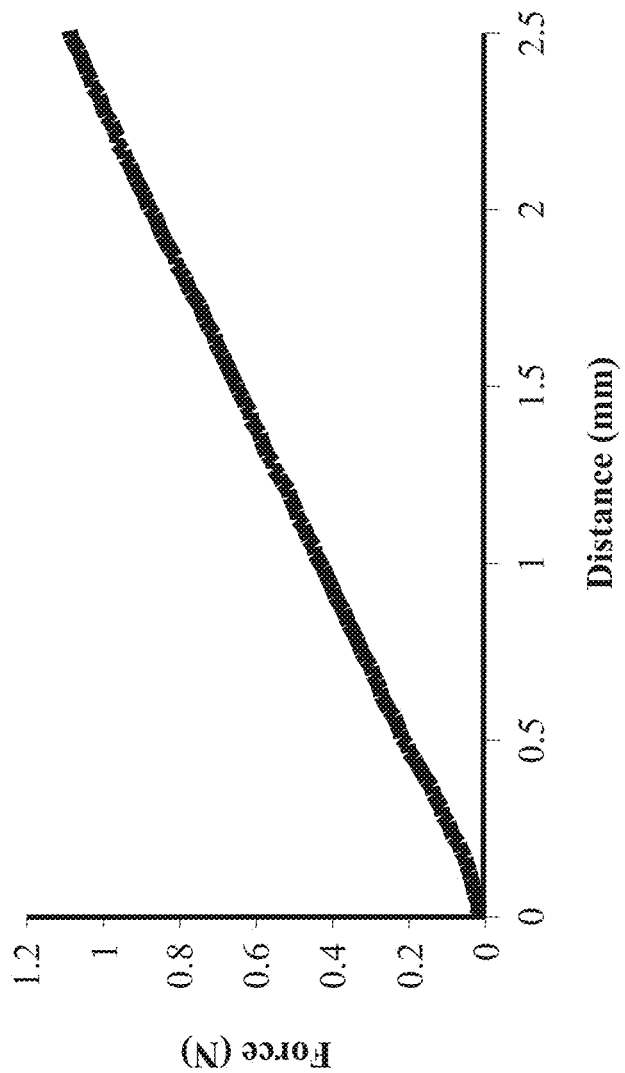
FIG. 2: Typical stress-strain curve (formulation 7 in simulated gastric fluid [SGF])

The strengths of the coacervate-like complexes of formulations 2-5, 2-6, and 2-7 formed post-immersion were measured using a TA-XT2 texture analyser equipped with a 25 kg load cell (Stable Micro Systems, Scarsdale, N.Y., USA) and a round cylindrical steel probe (2 mm ∅). The resistance of the samples to the compression of the probe was recorded. The pre-test speed was set up at 2.0 mm/s and the test speed at 0.2 mm/s. The post-test speed was set up at 1.0 mm/s. Acquisition rate was of 10 points per second. An example of stress-strain curve is given in FIG. 2. Furthermore, in order to evaluate the contribution of hydrophobic interactions and hydrogen bonding to the structure of the coacervate-like structures, experiments were repeated using SGF and SIF containing 2M of ethanol or 2M of urea, respectively. For each sample, the work of cohesion was calculated as the area under the stress-strain curve between 0 and 2.5 mm. Work of cohesion is expressed in mJ. Typical results are shown in Table 2. All experiments were repeated at least three times.

TABLE 2

Work of cohesion (in $10^{-4}$ mJ) for formulations 2-5, 2-6 and 2-7 in SGF or SGF/SIF in presence and the absence of chaotropic agents

| Formulation | pH 1.0 (SGF for 2 h) | | | pH 6.9 (SGF for 2 h, then SIF for 2 h) | | |
|---|---|---|---|---|---|---|
| | No chaotropic agent | Urea 2M | Ethanol 2M | No chaotropic agent | Urea 2M | Ethanol 2M |
| 2-5 | 4.7 ± 0.8 | 4.1 ± 0.3 | 3.9 ± 0.3 | 8.2 ± 0.1 | 7.0 ± 0.6 | 7.3 ± 0.4 |
| 2-6 | 7.2 ± 0.5 | 5.1 ± 0.3 | 5.1 ± 0.6 | 10.1 ± 0.1 | 4.3 ± 0.6 | 4.7 ± 0.2 |
| 2-7 | 12.6 ± 1.1 | 8.1 ± 0.7 | 4.7 ± 0.6 | 4.7 ± 0.4 | 3.0 ± 0.4 | 2.3 ± 0.6 |

After immersion in SGF for 2 h, the higher the ratio of polysaccharides to proteins used in the formulation, the higher the work of cohesion that was observed. This result indicates that higher ratios of polysaccharides (e.g., kappa-carrageenan) led to stronger coacervates. It also suggests that strength of the post-immersion complexes were related to polysaccharide-protein interactions, and further that an increase in polysaccharide to protein ratio in the formulations may favour protein/polysaccharide interactions at the expense of protein-protein interactions. In the presence of chaotropic agents, work of cohesion values tended to decrease. Thus, urea and ethanol both led to a decrease in strength of the coacervate-like complexes, suggesting that both hydrogen bonds and hydrophobic forces influence complex stabilization. Moreover, the higher the ratios of polysaccharides to proteins, the more pronounced the effect of the chaotropic agents. This result confirms that strength of the complexes strongly depends on protein/polysaccharide interactions, suggesting not only the formation of coacervates, but also that the strength of the coacervates formed is inversely proportional to the rate of release of the active ingredient. Without being bound by theory, by forming tighter and stronger complexes, coacervates may considerably slow down the release of active ingredients.

After immersion in SGF for 2 h followed by SIF for 2 h, increasing polysaccharide to protein ratio led to a slight increase of work of cohesion values (from formulation 2-5 to 2-6) before decreasing complexes' strength by approximately 50% in formulation 2-7. However, despite these small differences, the effect of the chaotropic agents were still particularly marked, suggesting that protein/polysaccharide interactions govern the strength of the coacervate-like complexes, even upon subsequent incubation in SIF.

Interestingly, while the dissociation constant of the sulphate groups of kappa-carrageenan is approximately equal to 3 (pKa~2.8) and the isoelectric point of the whey protein is approximately equal to 5 (pI~5.2), coacervate complexes remained intact upon incubation at pH 6.9 (SIF). Thus, the formation of coacervate-like complexes of formulation 2-5 to 2-6 post-immersion in SGF (and SGF/SIF) was somewhat unexpected, since the scientific literature consistently reports that stable protein/polysaccharide coacervates form in a pH range of between the pKa of the polysaccharides and the isoelectric point of the protein material (pI) (Syrbe et al., 1998; Tolstoguzov, 1997). Therefore, these results highlight the impact of protein/polysaccharide ratios on coacervate-like complex strength in both SGF (pH 1.0) and SIF (pH 6.9).

3.2 FTIR Analysis of Amide I' Region

Formulations were incubated for 2 h in 10 mL of $D_2O$ adjusted with DCl 0.5 M to pD 1.5 (pH 1.1), or in the same solution for 2 h and followed by in 10 mL of $D_2O$ adjusted to 7.3 (pH-6.9) using NaOD 0.5 M. Then, tablet surface was taken and was slightly pressed and analysed using a horizontal attenuated total reflectance (ATR) crystal (ZnSe). Infrared spectra were recorded with a Magna 560 Nicolet spectrometer (Madison, Wis., USA) equipped with a mercury-cadmium-telluride detector. The spectrometer was continuously purged with dried air. Each spectrum is the result of an average of 128 scans and apodised with a Happ-Genzel function. To study the amide I' region, subtractions and Fourier self-deconvolutions were performed using the Omnic™ software. Band narrowing was achieved with a full width at half of 18 $cm^{-1}$ and with a resolution enhancement factor of 2 $cm^{-1}$. All spectra were performed at least twice.

Figure 3:
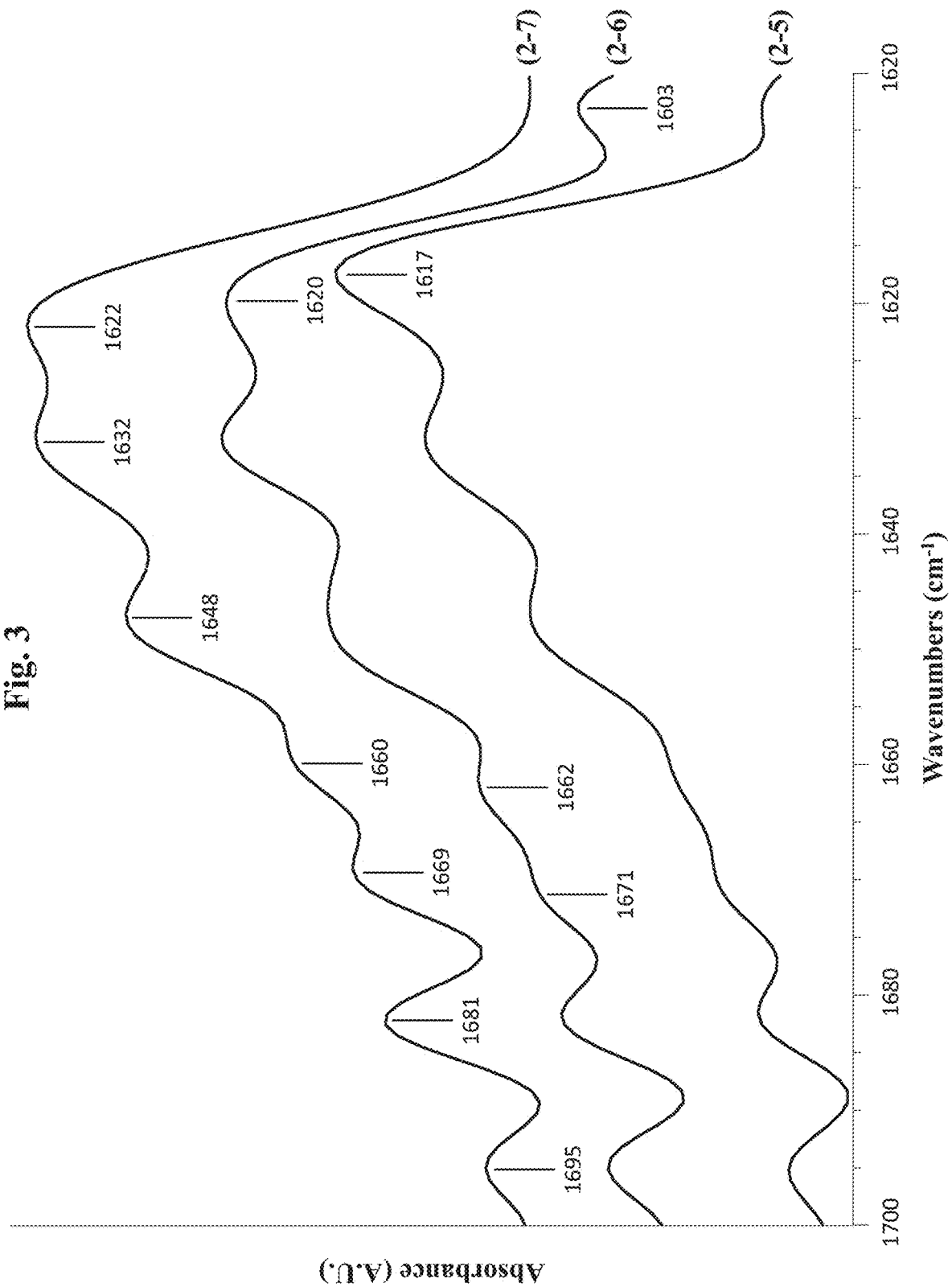
FIG. 3: Deconvoluted amide I' bands obtained from formulations 2-5, 2-6, and 2-7 after 2 h at pH 1.0 (SGF) or pH 6.9 (SIF).

FIG. 3 shows results from FTIR analyses and illustrates amide I' region for coacervates taken on the surface of tablets formulations 2-5, 2-6, and 2-7 subjected to dissolution testing as described in Example 3.1. Interestingly, no particular differences were observed between spectra obtained at acidic (SGF) or more neutral pH (SGF followed by SIF). Indeed, there was no observed difference in terms of the incidence on bands' position or intensity, by immersing formulations 2-5, 2-6, and 2-7 in SGF with or without subsequent immersion in SIF. These results suggest that coacervate-like complexes initially form upon contact of the protein/polysaccharide mixtures with SGF during the gastric phase, and that these complexes remain relatively structurally unchanged following subsequent exposure to SIF.

In more detail, FIG. 3 shows that all spectra were composed of eight components located at 1695 $cm^{-1}$, 1681 $cm^{-1}$, $1671^{-1}$, 1669 $cm^{-1}$, 1662-1660 $cm^{-1}$, 1648 $cm^{-1}$, 1632 $cm^{-1}$, 1622-1617 $cm^{-1}$ and 1603 $cm^{-1}$. Components located at 1632, 1662-1660, 1671-1669 and 1691 $cm^{-1}$ were attributed to intramolecular beta-sheets and unordered structures. The band located at 1648 $cm^{-1}$ was attributed to alpha-helices and unordered structures. The small shoulder at 1603 $cm^{-1}$ was attributed to amino acid side chain vibration. The amide I' maximum at around 1617-1622 $cm^{-1}$ is characteristic of the presence of intermolecular beta-sheet hydrogen bonds. Such a band is characteristic of protein-protein interactions. The frequency of this band seemed progressively shifted from 1617 $cm^{-1}$ (formulation 2-5) to 1622 $cm^{-1}$ (formulation 2-7) (Gilbert et al., 2005). This may be attributed to a weakening of protein-protein interactions while polysaccharide concentration is increased in tablets. Without being bound by theory, this phenomenon may be related to the intercalation of the polysaccharide (kappa-carrageenan) molecules between protein chains. This result is consistent with our other observations that an increase in polysaccharide ratio in tablets favor protein-polysaccharide interactions at the expense of protein-protein interactions. Finally, the less pronounced component located at 1681 $cm^{-1}$ would be consistent with the presence of intermolecular antiparallel beta-sheets.

In general, these results provide compelling evidence of the formation of protein/polysaccharide complex coacervates in situ upon immersion of the formulations in SGF (pH 1.0), and that the coacervates formed in situ are able to sufficiently withstand subsequent exposure to SIF (pH 6.9) to achieve modified/slowed release of the active ingredient. Furthermore, the observation that the coacervate strength and rate of release of the active ingredient may be controlled by simply varying the ratio of protein/polysaccharide mixture in the formation, suggests that it is possible to customize active ingredient release rate and/or duration of an active ingredient by varying the biopolymer ratios in the oral formation, thereby providing the basis for a versatile coacervate-based oral delivery system that is readily adaptable to the release profile desired.

Example 4

Coacervate-Forming Protein/Polysaccharide Powder Mixtures Are Suitable for Capsule Formulations Capsules are one of the most commonly employed solid oral dosage forms for the delivery of active ingredients and present some advantages over tablets for certain formulations. In this Example, coacervate-forming protein/polysaccharide powder mixtures were added to capsule formulations to assess their suitability for use in such formulations.

4.1 Capsule Preparation

Cellulose-based capsules were used (HPMC, K-Caps™). Empty capsules were manually filled with mixes containing protein/polysaccharide powders consisting of pea protein powder (The Scoular Company, Nebr., USA) mixed with a carrageenan (supplier A)-xanthan (Supplier D) powder, microcrystalline cellulose (MCC), and an active ingredient (caffeine or the probiotic *P. acidilactici*). Protein:polysaccharide mixtures were at a weight ratio of 85:15. Then, capsules were manually closed with the cap. Capsule in vitro release performances were subsequently tested.

4.2 Capsule In Vitro Release Performance

In vitro release performances of capsules were tested using a dissolution apparatus SR6 Dissolution test station (Hanson Research Corp., Chatsworth, Calif.). For each formulation, six capsules were tested following USP <724> for the dissolution specifications for delayed-release dosage forms. Briefly, a typical dissolution experiment consisted in the immersion of capsules into a simulated gastric fluid (SGF) for 2 h followed by the immersion of the capsules into a simulated intestinal fluid (SIF) until complete dissolution. Paddle speed was set at 65 rpm and temperature was maintained at 37° C. Vessel volume was 1000 mL.

SGF consisted in a diluted HCl (37%) solution, pH 1.0, containing 2 g/L of NaCl and 0.1 g/L of pepsin. SIF consisted in a $NaH_2PO_4$ buffer (50 mM), pH 6.9, containing 0.5 g/L of pancreatin. Experiments were repeated at least two times. During every experiment, capsule immersion was ensured using stainless steel sinkers with six spirals.

For the probiotic, *P. acidilactici* strain survival was measured after 1 h and 2 h of immersion in SGF, followed by the capsules being transferred and completely dissolved in 150 mL of sterile SIF. Subsequently, dilutions were performed, and strains were cultured using MRS agar in aerobic conditions at 37° C. for 48 h. Microbial counts were then performed.

For caffeine, release was followed measuring absorbance at 271 nm using a UV160A UV-vis spectrophotometer (Shimadzu, Kyoto, Japan). Prior to analysis, samples were filtered.

4.3 Results

Probiotics Survival

Tested formulations, expressed in % weight, are given in Table 3. Three different formulations containing respectively 0%, 35% and 50% w/w of protein/polysaccharide powder mixtures were prepared. Capsules' final weight was 500±15 mg.

TABLE 3

*P. acidilactici* capsule formulations tested

| Formulation (in % w/w) | 4-1 | 4-2 | 4-3 |
|---|---|---|---|
| Protein/polysaccharide powder mixture* | 0 | 35 | 50 |
| MCC | 75 | 40 | 25 |
| *P. acidilactici* | 25 | 25 | 25 |

*pea protein powder:carrageenan/xanthan powder (weight ratio 85:15).

Figure 4:
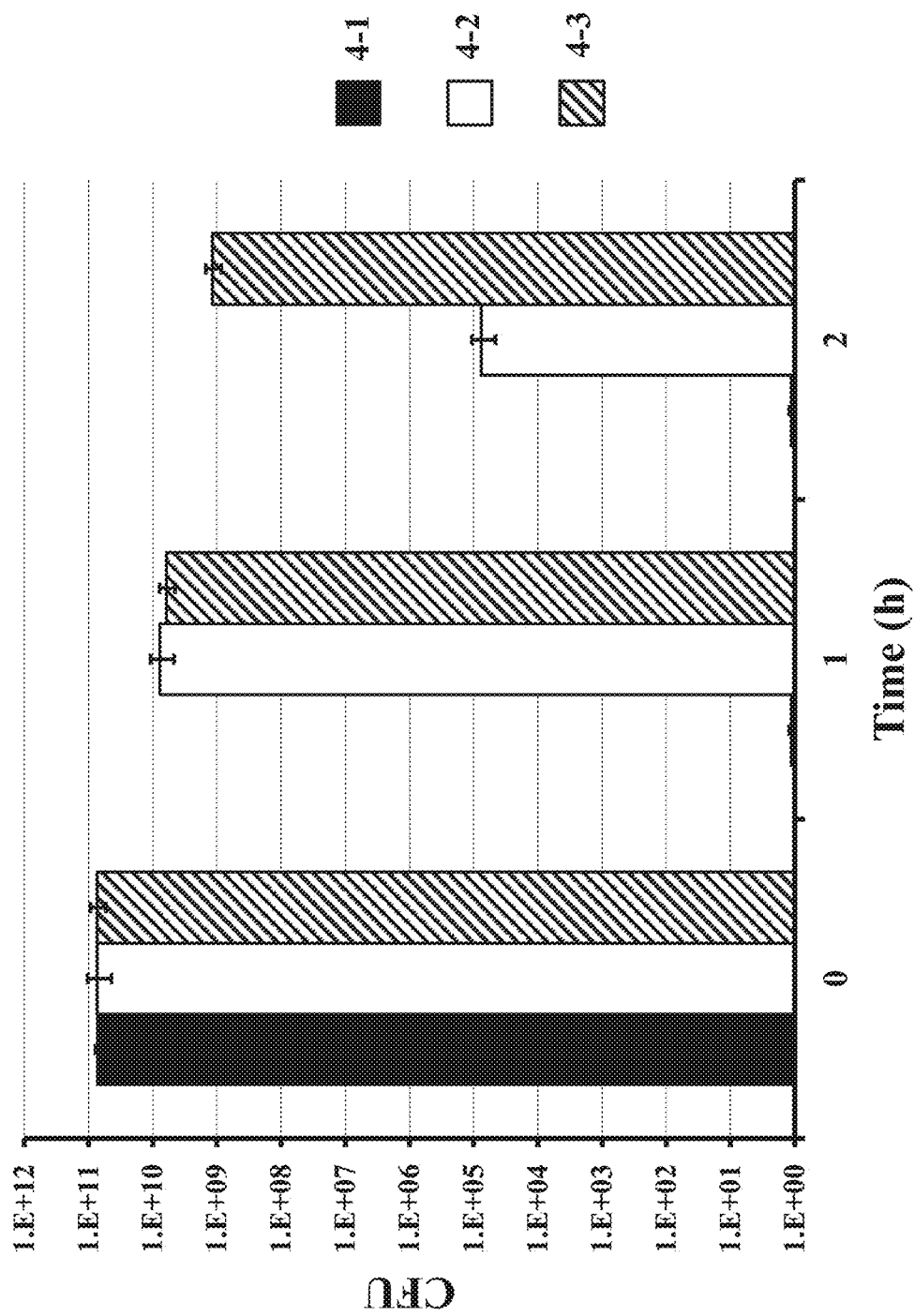
FIG. 4: *Pediococcus acidilactici* survival following immersion of formulations 4-1, 4-2, and 4-3 for 1 or 2 h in simulated gastric conditions, following United States Pharmacopeia (USP) <711> specifications.

Results for probiotic survival are shown in FIG. 4. Capsules opened after approximately 12 minutes in SGF. Capsules containing only microcrystalline cellulose (MCC) (formulation 4-1) showed quick dissolution and *P. acidilactici* survival was not detectable after 1 h in the SGF. In contrast, formulations 4-2 and 4-3 showed significant survival after the gastric step. After 1 h, formulations 4-2 and 4-3 yielded viable CFUs of $7.4\pm1.8\times10^9$ and $6.2\pm2.0\times10^9$, respectively. After 2 h, the CFUs were $7.7\pm3.1\times10^4$ for formulation 4-2, and $1.2\pm0.1\times10^9$ for formulation 4-3. Strikingly, although control formulation 4-1 (lacking the coacervate-forming proteins-polysaccharide mixture) exhibited a 10.5-log decrease in viability, formulations 4-2 and 4-3 showed only a 1-log decrease after 1 h in SGF.

Figure 5:
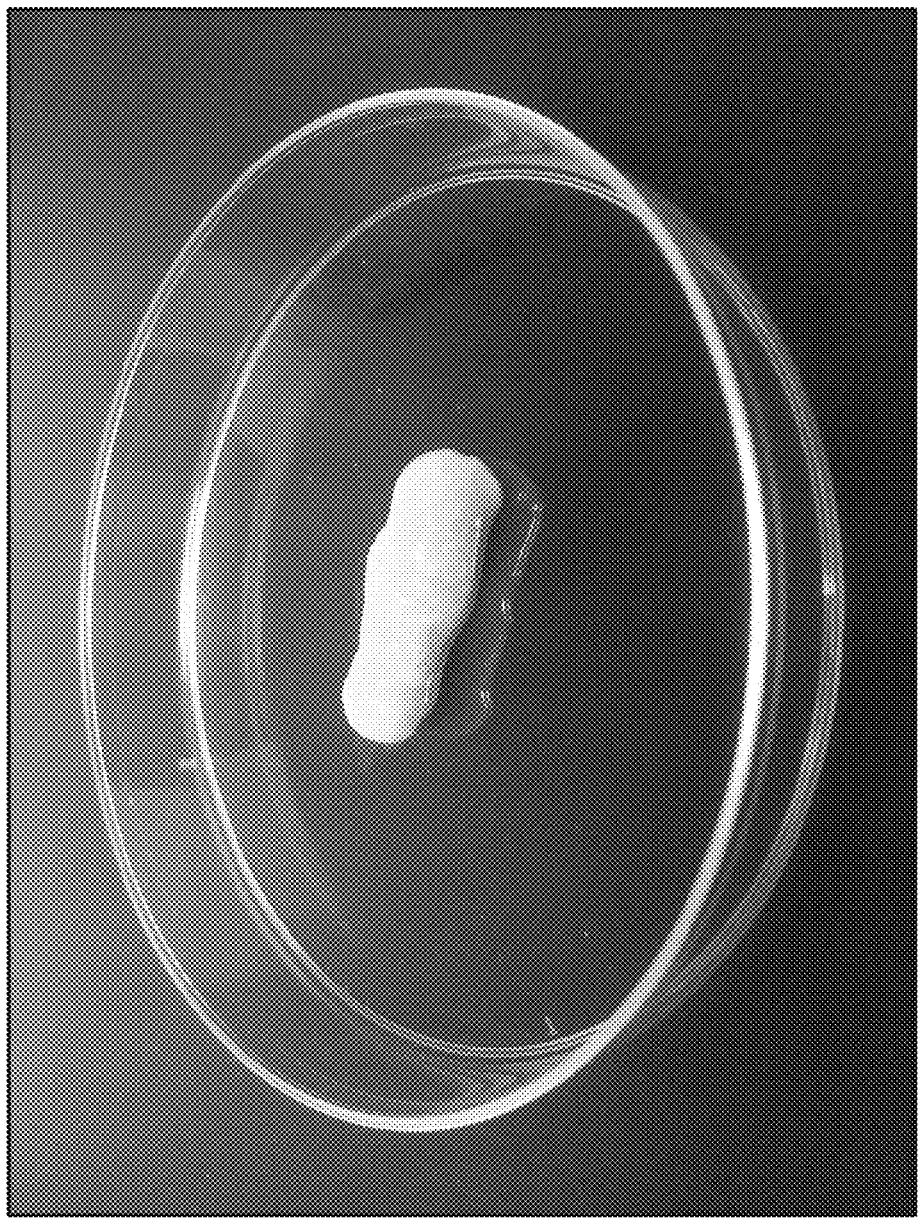
FIG. 5: Remaining capsule content after immersion of formulation 4-3 for 2 h in SGF: protein/polysaccharide mixture forms a complex coacervate fitting the shape of the capsule.

The gastric protection results observed are explained by the formation of coacervates by the protein/polysaccharide mixture when the capsules started to open. Indeed, while simulated gastric fluid penetrates the capsules and the capsules start to dissolve, the protein/polysaccharide mixture begins to form coacervates in situ (as characterized in Example 3 for post-immersion tablets), leading to the formation of a complex coacervate fitting the shape of the capsule (see FIG. 5).

Thus, these results demonstrate the suitability of coacervate-forming protein/polysaccharide mixtures for gastric protection, as well as for modified release of active ingredients.

Caffeine Release

The same experiments as with *P. acidilactici* were performed, replacing with caffeine as the active ingredient. Two formulations were tested: one containing a protein/polysaccharide mixture, the other containing only filler (MCC). Capsule formulations that were tested are described in Table 4. Capsule weight was approximately 500 mg.

TABLE 4

Caffeine capsules formulations tested (in % w/w)

| Formulation (in % w/w) | 4-4 | 4-5 |
|---|---|---|
| Protein/polysaccharide powder mixture* | 0 | 35 |
| MCC | 75 | 40 |
| Caffeine | 25 | 25 |

*pea protein powder:carrageenan/xanthan powder (weight ratio 85:15).

Figure 6:
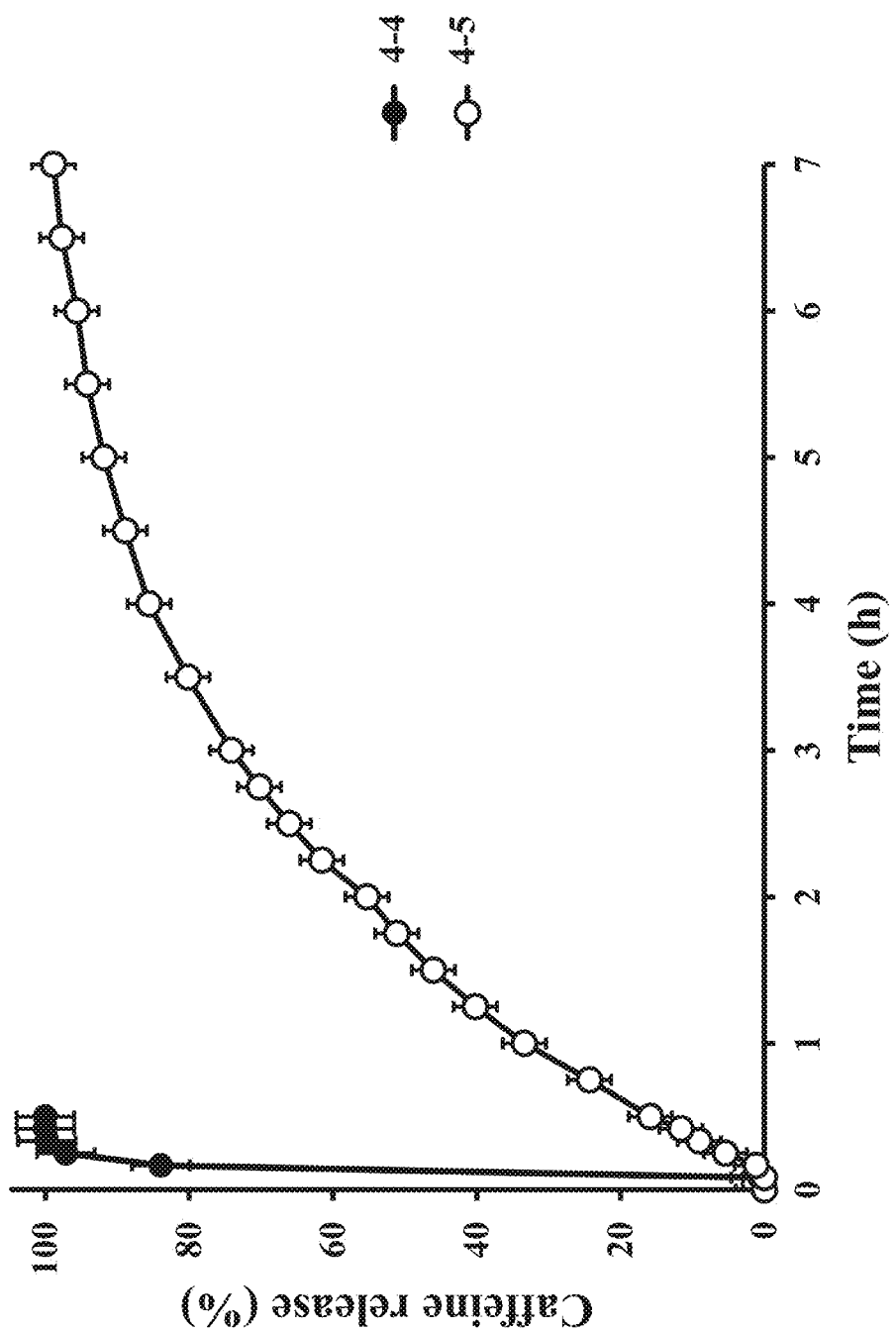
FIG. 6: Caffeine release profiles obtained from formulation described in Table 4.

Release profiles obtained from each formulation are given in FIG. 6. For both formulations, caffeine release began after 5 to 10 min of experiment. This period corresponds to the time required by the capsule to start to dissolve and expose its contents to the surrounding fluid.

In the case of the formulation containing only MCC as a filler (formulation 4-4), a rapid release of caffeine was observed and 97% of the caffeine was released after 15 min in SGF.

In the case of formulation 4-5 containing 35% w/w of the protein/polysaccharide mixture, caffeine release was extended for several hours and 100% release was observed after approximately 6-7 hours. This result is consistent with that for probiotics and demonstrates that the protein/polysaccharide powder mixture forms a complex that protects the active ingredient from acidic conditions, and is able to extend the release of the active ingredient from several minutes to several hours.

4.4 Discussion

Results in this Example show that the use of in situ coacervate-forming protein/polysaccharide powder mixtures are suitable for capsule formulations in addition to tablet formulations. Indeed, their use in capsules led to modified-release profiles where active ingredient dissolution was extended over several hours, and also provided protection of the active ingredient in simulated gastric conditions.

Figure 7:
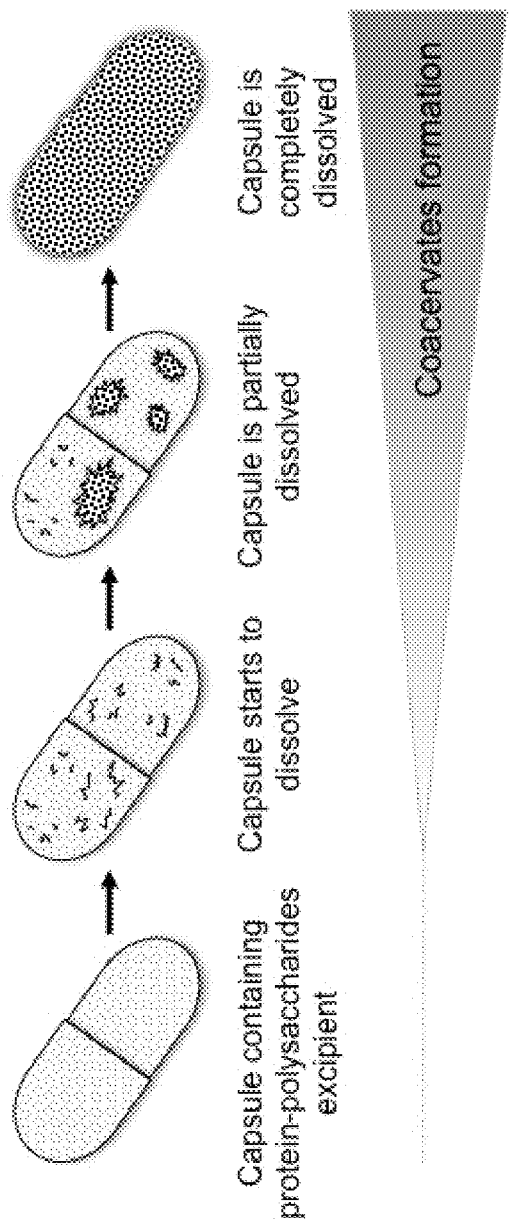
FIG. 7: Schematic representation of the process of capsule dissolution and coacervate-forming complex formation.

Dissolution of gelatin- or cellulose-based capsules is not an instantaneous and total process. Without being bound by theory, it is possible that when capsule dissolution starts, surrounding fluid penetrates the capsule and leads to the simultaneous dissolution of the active ingredient and protein/polysaccharide complex coacervate formation. This process continues until the capsule is completely dissolved, leading to the formation of a structure that fits the shape of the capsule (e.g., see FIG. 5). The process of capsule dissolution and coacervate-forming complex is shown schematically in FIG. 7.

Using standard technologies that are currently available, capsules are typically manufactured using gelatin or cellulose. Once filled with a given formulation containing an active ingredient, additional processing steps and additives are required, such as applying a coating on the capsules' surface to obtain gastric protection and/or a modified release profile. Strikingly as shown herein, the in situ coacervate-forming protein/polysaccharide powder mixtures were able to provide both gastric protection and modified release of the active ingredient in the absence of additional processing steps, such as without adding a further coating (e.g., enteric coating) to the capsule.

Example 5

Parameters Governing Performance of Polysaccharide Powders in Oral Delivery Systems Based on In Situ Forming Protein/Polysaccharide Coacervates Examples 1-4 demonstrate the suitability of coacervate-forming protein/polysaccharide powder mixtures for oral delivery systems. More specifically, Examples 2 and 3 demonstrate coacervate formation associated with modified release of active ingredients with both native and denatured whey proteins, while Example 4 demonstrates comparable results with pea protein powder, indicating that suitable coacervate formation is achievable using protein powders from different sources. In each of Examples 2-4, suitable coacervate formation was demonstrated using the polysaccharide kappa-carrageenan from the same supplier (supplier A). However, extensive empirical dissolution testing using different types of polysaccharides (i.e., other than kappa-carrageenan) and even the same type of polysaccharide from different suppliers (e.g., kappa-carrageenan obtained from different suppliers) yielded unpredictable results in terms of coacervate formation and gastric protection/modified release. (No such unpredictable results were observed with respect to the protein powders employed from different suppliers, which all had more uniform flour-like textures.) For example, it was observed that kappa-carrageenan powder obtained from supplier A was able to form a complex coacervate in situ that provided gastric protection, but that kappa-carrageenan from supplier B was not able to do so. Furthermore, without subjecting the oral formulations to empirical dissolution testing, it was not possible to reliably predict beforehand (e.g., based on supplier-provided product specification sheets) which polysaccharides from which suppliers would form successful coacervates in situ. These unpredictable results led to extensive efforts to identify objective and measurable parameters that could reliably predict polysaccharide powders that function in the in situ coacervate-forming oral delivery systems of Examples 1-4. These efforts resulted in a set of measurable/calculatable parameters of the polysaccharide powder (i.e., Dynamic cohesive index, angle of repose, Carr index/compressibility, and Hausner ratio) that could be used to reliably predict its suitability for the in situ coacervate-forming oral delivery systems described herein. The results shown below in the present Example demonstrate the foregoing.

5.1 Tablet Manufacturing

Tablets were prepared by direct compression using a TDP-6 single punch press (Yangzhou Nuoya Machinery co. Ltd., Jiangju, China). Powders were weighed and subsequently mixed together in a mortar prior to tabletting. Tablet diameters and thicknesses were respectively 11.2 mm and 6.5 mm. 24 h after manufacture, tablet hardness was measured following USP <1217>, using a Tablet Hardness Tester YD-1 (Minsheng Pharmaceutical Machinery Ltd., Shanghai, China). Hardness was between 7 and 9 kp.

In this Example, thermally denatured pea proteins were chosen as the protein powder, and various polysaccharides from different suppliers were formulated in parallel. The general composition of the tablet formulations is shown in Tables 5 and 6.

TABLE 5

Tablet formulations tested in this Example

|  | Ingredient | Quantity (mg) |
|---|---|---|
| Protein/polysaccharide powder mixture | Pea protein powder | 130 |
|  | Polysaccharide powder (see Table 6) | 35 |
| Active ingredient | *Pediococcus acidilactici* | 110 |
| Additives | MCC | 115 |
|  | Magnesium stearate | 6 |
|  | Silicon dioxide | 6 |
|  | Stearic acid | 50 |

5.2 Erosion of Tablets

Erosion of tablets was followed using a disintegration apparatus (Tianjin Guoming Medicinal Equipment Co., Tianjin, China). Tests were performed following USP specifications <2040>. In a typical experiment, one tablet was placed in each of the three tubes of the basket. No sinkers were used. Then, the apparatus was operated with SGF at 37° C. as the immersion fluid for 1 h. Experiments were conducted at least in triplicate. Disintegration was followed gravimetrically. After 1 h, the erosion rate of the tablet was measured and expressed as the % of disintegrated tablet (D %). If the tablet was completely disintegrated before the end of the experiment, its disintegration time was noted (D %). Table 6 illustrates D % and DT values for the different tested tablets.

5.3 Polysaccharide Powder Characteristics

Polysaccharide powders were characterized by measuring their angle of repose, dynamic cohesive index, their bulk and tapped densities, their compressibility index (Carr index), and their Hausner ratio. Powder properties were determined following USP <1174> specifications. Dynamic cohesive index was estimated using the correlation existing between α value (angle of repose) and the cohesive index (Boschini et al., 2015).

These properties are indicators of powder flowability, texture, and cohesiveness. Angle of repose values (α) and powder cohesive index are strongly correlated (Boschini et al., 2015), thus, α values were used to determine the corresponding cohesive index value.

5.4 Results

*P. acidilactici* was selected as the active ingredient. All tablets had the same formulations (see Table 5), wherein only the polysaccharide type or origin varied (see Table 6).

TABLE 6

Tablet disintegration D % and DT

| Polysaccharide powder | Supplier | Formulation | % Tablet disintegration after 1 h in SGF | Time until complete tablet disintegration (if <1 h) |
|---|---|---|---|---|
| Kappa-carrageenan | B | 5-1 | 100% | 32 min |
|  | A | 5-2 | 5% | — |
| Xanthan gum | B | 5-3 | 3% | — |
|  | C | 5-4 | 57% | — |
|  | D | 5-5 | 7% | — |
|  | E | 5-6 | 100% | 12 min |
| Gellan | B | 5-7 | 100% | 29 min |
|  | G | 5-8 | 100% | 38 min |
| Pectin LM | B | 5-9 | 8% | — |
| Pectin HM | B | 5-10 | 22% | — |
| Agar | B | 5-11 | 15% | — |
| Alginate | A | 5-12 | 11% | — |
|  | B | 5-13 | 3% | — |
|  | F | 5-14 | 4% | — |

The results in Table 6 showed that the formulations 5-2, 5-3, 5-5, 5-9, 5-10, 5-11, 5-12, 5-13, and 5-14 (bolded) exhibited significant resistance following 1 h exposure to SGF, suggesting that these formulations would be suitable for gastric protection/modified release applications. In contrast, formulations 5-1, 5-6, 5-7, and 5-8 provided virtually no gastric resistance following 1 h exposure to SGF, precluding their use in gastric protection/modified release oral delivery systems. Formulation 5-4 exhibited intermediate gastric resistance to SGF.

Surprisingly, formulations 5-1 and 5-2 exhibited completely opposite erosion results (100% vs 5%) despite consisting of all the same ingredients. In fact, the only difference between formulations 5-1 and 5-2 was the source of the polysaccharide (kappa-carrageenan; supplier A vs B). Similarly, formulations 5-3, 5-4, 5-5, and 5-6, differ only in the source of the polysaccharide (xanthan gum, suppliers B, C, D, or E), yet each formulation gave vastly different erosion results ranging from 3% to 100%. Moreover, the results could not be explained from the specification sheets provided by the various suppliers for each of the polysaccharide powders tested. Thus, the characteristics and properties of each of the polysaccharide powders were studied in order to attempt to understand the contradictory results from erosion testing.

For each of the polysaccharide powders, different parameters were compared, including powder densities, compressibility, Hausner ratio, angle of repose, cohesiveness, pH in solution and viscosity (which is, among other things, related to polymer molecular weight). Moreover, it is reported in the literature that low salt concentrations promote interactions while high salt concentrations tend to diminish or suppress coacervation (Schmitt, 2000; de Kruif et al., 2004). Thus, salt content, based on each of the polysaccharide powders' Certificate of analysis, were also compared. These data are shown ranked in order of disintegration efficiency in Table 7.

TABLE 7

Characteristics of polysaccharide powders (5-1 to 5-6) sorted based on D (%)/DT (min)

| | Formulation: | | | | | |
|---|---|---|---|---|---|---|
| | 5-3 | 5-2 | 5-5 | 5-4 | 5-1 | 5-6 |
| Polysaccharide [Supplier] | Xanthan gum [B] | kappa-carrageenan [A] | Xanthan gum [D] | Xanthan gum [C] | kappa-carrageenan [B] | Xanthan gum [E] |
| D (%) (DT in mins) | 3% | 5% | 7% | 57% | 100% (32 min) | 100% (12 mm) |
| pH (0.2% in water) | 6.7 | 6.9 | 6.7 | 6.9 | 6.9 | 6.7 |
| Viscosity (0.2% w/w) (cP) | 169 ± 12 | 14 ± 1 | 186 ± 10 | 181 ± 11 | 15 ± 1 | 172 ± 8 |
| [Salts] (% w/w)* | 4.3% | 9.8% | 9.6% | 9.2% | 4.3% | 2.5% |
| Tap density (g/cm$^3$) | 0.80 ± 0.00 | 0.58 ± 0.02 | 0.85 ± 0.02 | 0.80 ± 0.00 | 0.76 ± 0.02 | 0.88 ± 0.02 |
| Bulk density (g/cm$^3$) | 0.56 ± 0.05 | 0.43 ± 0.01 | 0.51 ± 0.02 | 0.68 ± 0.01 | 0.59 ± 0.02 | 0.75 ± 0.02 |
| Hausner ratio | 1.45 ± 0.12 | 1.34 ± 0.01 | 1.65 ± 0.10 | 1.17 ± 0.02 | 1.28 ± 0.03 | 1.17 ± 0.05 |
| Carr index/ compressibility (%) | 31 ± 6 | 25 ± 1 | 39 ± 4 | 15 ± 2 | 22 ± 2 | 15 ± 4 |
| Angle of repose | 51 ± 5 | 55 ± 3 | 48 ± 3 | 34 ± 2 | 32 ± 7 | 28 ± 2 |
| Dynamic cohesive index | 30-40 | 30-40 | 30-40 | 5-10 | 5-10 | <5 |

*According to certificate of analysis from supplier.

The results shown in Table 7 reveal that tablet erosion in SGF (D/DT) could not reliably be predicted from polysaccharide powder parameters such as pH, viscosity, salt concentration, tap density, or bulk density. In fact, most polysaccharide powders had very different salt concentrations. For example, while the polysaccharide powders of formulations 5-3 and 5-1 had the same salt content (4.3%), formulations 5-3 and 5-1 performed very differently in erosion testing (3% vs. 100%). Considering the well-known effect of ionic force and counter ions on protein/polysaccharide complex formation, these results were quite surprising.

Interestingly, however, polysaccharide powders with higher Hausner ratios and Carr index/compressibility (indicative of powder flowability) were those that tended to form more slowly disintegrating tablets (and vice versa). These results suggest that polysaccharide powders which tend to aggregate with proteins to form sufficiently strong coacervates in situ should be cohesive (have poor flowability), and conversely, that granular or sandy powders (e.g., which are without fine particles or fibers), are less capable of interacting with the protein powders upon exposure to SGF, thereby resisting erosion.

Angle of repose measurements showed that polysaccharide powders with higher angle values were more capable of complexing with protein powders upon exposure to SGF, thereby resisting erosion (and vice versa). Angle of repose values indicate that cohesive powders were suitable for slowly disintegrating oral (or tablet/capsule) formulations and, on the contrary, that free flowing powders would not. This result goes hand in hand with those obtained from compressibility index and Hausner ratio values.

Finally, angle of repose can be directly related to dynamic cohesive index (Boschini et al., 2015). It appears that polysaccharide powders with a dynamic cohesive index below 10 were not capable of aggregating with proteins, while polysaccharides powders with a cohesive index over 10 are those susceptible to interact with protein materials and form coacervates.

Interestingly, the least erosion resistant formulations were obtained using the polysaccharide powders having a cohesive index below 5 and angles of repose below 30 (e.g., see formulation 5-6 in Table 7 exhibiting complete disintegration after only 12 min). Conversely, progressively more erosion resistant formulations were obtained with polysaccharide powders of increasing cohesive index and angle of repose (Table 7).

Table 8 summarizes for each tested polysaccharide powder Hausner ratio, Carr index, angle of repose, dynamic cohesive index and their corresponding disintegration time in SGF (if applicable) and disintegration % at the end of the gastric step. Overall, parameters relating to polysaccharide powder cohesiveness were observed to reliably predict the polysaccharide powder's suitability to form coacervates with proteins in situ, in the context of oral delivery systems described herein. More specifically, polysaccharide powders having higher dynamic cohesive index, angle of repose, Hausner ratio, and Carr index (compressibility index) were observed to result in the formation of stronger coacervates in situ upon exposure to SGF, thereby providing greater gastric protection and/or slower release of the active ingredient.

Interestingly, for suitable polysaccharides, increasing their concentrations in the tablet formulations led to an increase in disintegration time as well as a decrease in disintegration % at the end of simulated gastric step (results not shown).

TABLE 8

Coacervate-forming characteristics of polysaccharide powders sorted based on D (%)/DT (min)

| Polysaccharide | Supplier | Formulation | Hausner ratio | Carr index/ compressibility (%) | Angle of repose | Dynamic cohesive index | D % (DT in min) |
|---|---|---|---|---|---|---|---|
| Xanthan gum | B | 5-3 | 1.45 | 31 | 51 | 30-40 | 3% |
| Alginate | B | 5-13 | 1.62 | 38 | 42 | 20-30 | 3% |
| Alginate | F | 5-14 | 1.72 | 42 | 47 | 30-40 | 4% |
| Kappa-carrageenan | A | 5-2 | 1.34 | 25 | 55 | 30-40 | 5% |
| Xanthan gum | D | 5-5 | 1.65 | 39 | 48 | 30-40 | 7% |
| Pectin LM | B | 5-9 | 1.32 | 24 | 39 | 10-20 | 8% |
| Alginate | A | 5-12 | 1.53 | 35 | 43 | 20-30 | 11% |
| Agar | B | 5-11 | 1.63 | 39 | 44 | 20-30 | 15% |
| Pectin HM | B | 5-10 | 1.51 | 34 | 45 | 30-40 | 22% |
| Xanthan gum | C | 5-4 | 1.17 | 15 | 34 | 5-10 | 57% |
| Gellan | G | 5-8 | 1.23 | 18 | 28 | 5-10 | 100% (38 min) |
| Kappa-carrageenan | B | 5-1 | 1.28 | 22 | 32 | 5-10 | 100% (32 min) |
| Gellan | B | 5-7 | 1.19 | 23 | 33 | 5-10 | 100% (29 min) |
| Xanthan gum | E | 5-6 | 1.17 | 15 | 28 | <5 | 100% (12 min) |

Example 6

Conditioning of Polysaccharide Powder for Increased Coacervate Formation and Improved Gastric Protection The results in Example 5 demonstrate that polysaccharide powders having higher cohesiveness (e.g., higher dynamic cohesive index, angle of repose, Hausner ratio, and Carr index) formed stronger coacervates in situ upon exposure to SGF, thereby providing greater gastric protection and/or slower release of the active ingredient. In Example 6, we demonstrate that a polysaccharide powder having low cohesiveness and providing poor gastric protection in the context of oral delivery systems described herein, can be conditioned for increased cohesiveness, and that this conditioning results in dramatically improved gastric protection.

Xanthan gum powder from supplier E (5-6) was selected since it provided the least gastric protection (100% disintegration in 12 min) amongst all the polysaccharide powders shown in Table 8. We attempted to modify the physical properties of the xanthan gum powder from supplier E as follows. A solution at 2% (w/v) was prepared in double distilled water and was subsequently lyophilized. Following lyophilization, the powder was over-dried for five days at 60° C. and was then grinded. After grinding, polysaccharide powders were sifted through a No. 20 mesh (0841 μm). Table 9 illustrates the powder characteristics before and after conditioning Then, tablets were manufactured into formulations as described in Table 5, with each xanthan gum powder (original and modified), and tested using a disintegration apparatus as described in Example 5. Table 10 illustrates results obtained from each polysaccharide.

TABLE 9

Polysaccharide properties before and after conditioning

| | Unconditioned xanthan gum powder | Conditioned xanthan gum powder |
|---|---|---|
| Tap density (g/cm³) | 0.88 ± 0.02 | 0.52 ± 0.04 |
| Bulk density (g/cm³) | 0.75 ± 0.02 | 0.27 ± 0.02 |
| Hausner ratio | 1.17 ± 0.05 | 1.92 ± 0.12 |
| Carr index/compressibility (%) | 15 ± 4 | 48 ± 3 |
| Angle of repose | 28 ± 2 | 51 ± 4 |
| Dynamic cohesive index | <5 | 30-40 |

As shown in Table 9, conditioning of the xanthan gum powder resulted in decreased density (bulk and tapped) and a marked increase in parameters relating to greater powder cohesiveness (Hausner ratio, Carr index, angle of repose, and dynamic cohesive index). The conditioned xanthan gum powder also resulted a noticeably more fluffy powder. As shown in Table 10, a formulation using the conditioned xanthan gum powder resulted in tablets with very low disintegration rate in simulated gastric step (only 1% measurable).

TABLE 10

Tablet disintegration parameters

| | D % | DT (min) |
|---|---|---|
| Unconditioned xanthan | 100% | 12 min |
| Conditioned xanthan | 1% | — |

Example 7

Protein Material Type and Its Effect on Tablet Disintegration and Probiotic Survival In the present Example, we focused on the effect of protein type on the tablet release properties of different formulations. To do so, a probiotic formulation containing a *Lactobacillus helveticus* was made including different protein source materials (Table 11). Six different protein materials from eight different suppliers were test. For each protein type, post-SGF disintegration % was measured 0 after 60 min in a disintegration apparatus (as described in Example 5). At the end of the gastric step, tablets were transferred in 750 mL of a simulated intestinal fluid (SIF) consisting of a $KH_2PO_4$ buffer (50 mM), pH 6.9, containing 0.5 g/L of pancreatin. For each tablet, disintegration was assessed and disintegration time was measured. Subsequent to disintegration, CFUs were measured and were compared to initial counts in order to evaluate cell survival %. All experiments were performed twice, and the results are shown in Table 12.

TABLE 11

Tested formulations

| | Ingredient | Quantity (mg) |
|---|---|---|
| Protein/polysaccharide powder mixture | Native protein powder | 150 |
| | Polysaccharide powder xanthan:alginate (80:20) | 40 |
| Active ingredient | *Lactobacillus helveticus* | 140 |
| Additives | MCC | 335 |
| | Silicon dioxide | 5 |
| | Stearic acid | 30 |

TABLE 12

Post SGF disintegration %, Disintegration time (SIF) and probiotic survival rate as a function of protein type

| Protein Material | Supplier | D % post SGF | DT (min) in SIF | Probiotic survival (%) |
|---|---|---|---|---|
| Pea protein | G | 3% | 131 ± 5 | 53 |
| Pea protein | H | 5% | 118 ± 7 | 45 |
| Pea protein | I | 3% | 133 ± 3 | 48 |
| Rice protein | J | 2% | 152 ± 3 | 51 |
| Rice protein | K | 2% | 154 ± 5 | 42 |
| Rice protein | L | 4% | 142 ± 4 | 55 |
| Rice protein | M | 3% | 144 ± 2 | 45 |
| Coconut protein | M | 4% | 98 ± 5 | 46 |
| Sacha inchi protein | M | 3% | 129 ± 3 | 41 |
| Tara protein | M | 0% | 172 ± 8 | 50 |
| Hemp protein | M | 9% | 44 ± 6 | 41 |
| Hemp protein | N | 3% | 105 ± 3 | 49 |

The results shown in Table 12 show that protein type and source did not appear to greatly influence tablet disintegration in SGF. Cell survival rate was only slightly influenced and, irrespective of protein type or source, *L. helveticus* showed post-SGF survival between 40 and 55% and was therefore protected against the gastric harsh conditions. This effect is associated with the buffering capacity of protein materials in these conditions. Furthermore, protein type appeared to have an impact on simulated intestinal disintegration duration. Faster disintegration was observed for hemp and coconut proteins, while longer disintegration time were observed for rice and tara proteins. Pea protein showed "intermediate" disintegration time in simulated intestinal fluids. Without wishing to be bound by theory, these results may be explained—at least in part—by the fact that the protein concentrate/isolate composition and protein primary structure (e.g., quantity of hydrophobic amino acids, and quantity of ionizable amino acids) can influence coacervate formation and their dissociation rate at pH 7.

Finally, the same formulations were tested by replacing *L. helveticus* with other actives ingredients (e.g., vitamin C, caffeine). Dissolution experiments also demonstrated that these proteins were suitable for prolonging active ingredient release in vitro through coacervation. Overall, these results demonstrate that coacervate formation is attainable using different protein materials and suppliers.

Example 8

Methods for Examples 9-22

8.1 Tablet and Capsule Preparation

Tablets were prepared by direct compression using a TDP-6 single punch press (Yangzhou Nuoya Machinery co.

Ltd., Jiangju, China). Powders were weighed and subsequently mixed together in a mortar prior to tableting. Tablet diameters and thicknesses were respectively 11.2 mm and 4.5-6.5 mm. 24 h after manufacturing, tablet hardness was measured following USP <1217>, using a Tablet Hardness Tester YD-1 (Minsheng Pharmaceutical Machinery Ltd., Shanghai, China). Hardness was between 5 and 9 kp. Each of the polysaccharide powders employed had angles of repose greater than 35, Hausner ratios greater than 1.18, Carr index/compressibility index greater than 15, and dynamic cohesive index greater than 10.

In the case of capsule formulations, once powder mixed, capsules were filled using a manual capsule-filling machine. All tests were performed using "vegetarian" (HMPC) capsules "0".

8.2 Tablet/Capsule Dissolution Properties

In vitro performance of tablet/capsule formulations was tested using a dissolution apparatus SR6 Dissolution test station, USP II (Hanson Research Corp., Chatsworth, Calif.). Guidelines described in USP <2040> (Disintegration and dissolution of dietary supplements) were followed.

During experiments, paddle speed was set at 60-100 rpm and the temperature was maintained at 37° C. Prior to measurements, samples were filtered, and background absorbance was subtracted. Release was followed by measuring the concentration of the active ingredient (AI) dissolved in the release medium as a function of time. Depending on the active ingredient, release measurements were performed by HPLC or directly by spectrophotometry.

Typical dissolution experiments consisted in the immersion of 3 tablet formulations into a simulated gastric fluid (SGF) for 2 h followed by the immersion of the tablets into a simulated intestinal fluid (SIF), until complete dissolution. In the case of capsule formulations, immersion was ensured using stainless steel sinkers with six spirals.

SGF consisted of a diluted HCl (37%) solution, pH 1.0, containing 2 g/L of NaCl and 0.1 g/L of pepsin. SIF consisted of a $KH_2PO_4$ buffer (50 mM), pH 6.9, containing 0.5 g/L of pancreatin. Experiments were repeated at least two times.

8.3 Tablet Disintegration Properties

Tablet disintegration was tested using a disintegration apparatus (Tianjin Guoming Medicinal Equipment Co., Tianjin, China). Tests were performed following USP specifications <2040> (Disintegration and dissolution of dietary supplements). In a typical experiment, one tablet was placed in each of the three tubes of the basket. Sinkers were not used. The apparatus was operated using SGF at 37° C. as the immersion fluid for 1 h. Tablets were then transferred into SIF until complete disintegration. Tablet disintegration was followed gravimetrically. Experiments were repeated at least two times.

8.4 Probiotic Survival

When the active ingredient (AI) was a probiotic or a mix of probiotics, a particular attention was given to post-gastric cell survival. Thus, at the end of the disintegration experiments, microbial counts were performed. Strains were cultured following adequate procedures.

In the case of yeasts, strains were cultured using a YPD agar. All samples were cultured in aerobic conditions and incubated at 30° C. for 48-72 h.

In the case of *lactobacillus/bifidobacterial*, strains were cultured using an MRS agar. All samples were cultivated in anaerobic conditions and incubated at 37° C. for 48-72 h.

8.5 Proteolytic Activity

Pancreatin proteolytic activity (%) was measured as follows: at the end of the simulated gastric step, pH was adjusted to 7-7.5, tablet formulations were disintegrated using a rotor-stator homogenizer and 500 mg of native whey proteins were added. After 4 hours of incubation at 37° C., proteolysis was measured by dosing free amino groups, using OPA (orthophthadialdehyde) reagent. Experiments were done using the same amount of unencapsulated/unprotected pancreatin, with (negative control) or without (positive control) simulating a gastric passage. Proteolytic Activity (%) was determined by calculating the ratio of free amino group concentration for a given tablet formulation to the positive control.

Example 9

Probiotic Tablet Formulation and Release

Figure 8B:
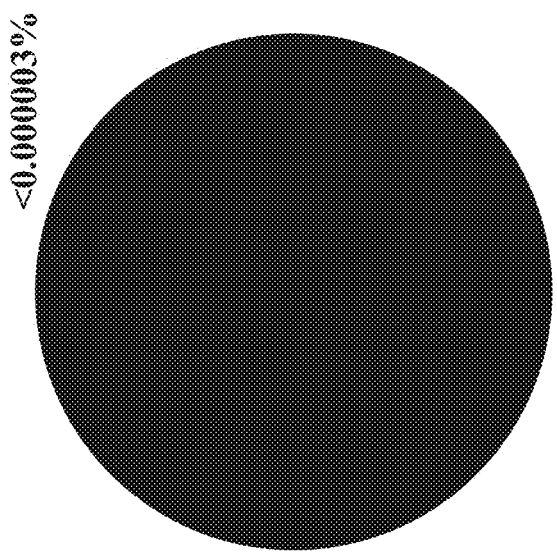
FIG. 8B: Survival of the probiotic strain alone (unformulated).
Figure 8A:
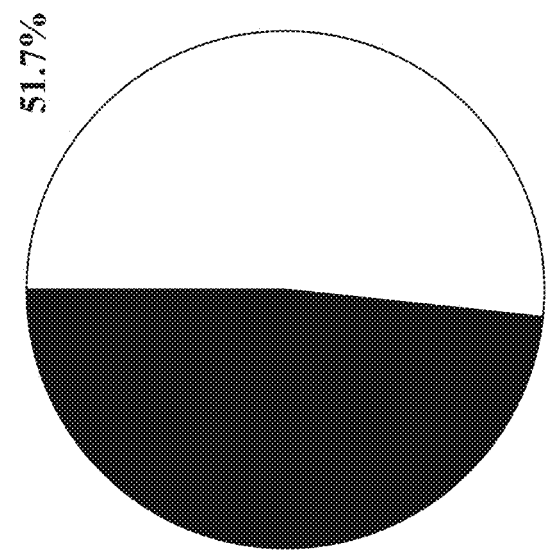
FIG. 8A: Post-gastric survival of probiotic strains obtained from the formulation described in Table 13.
Figure 9:
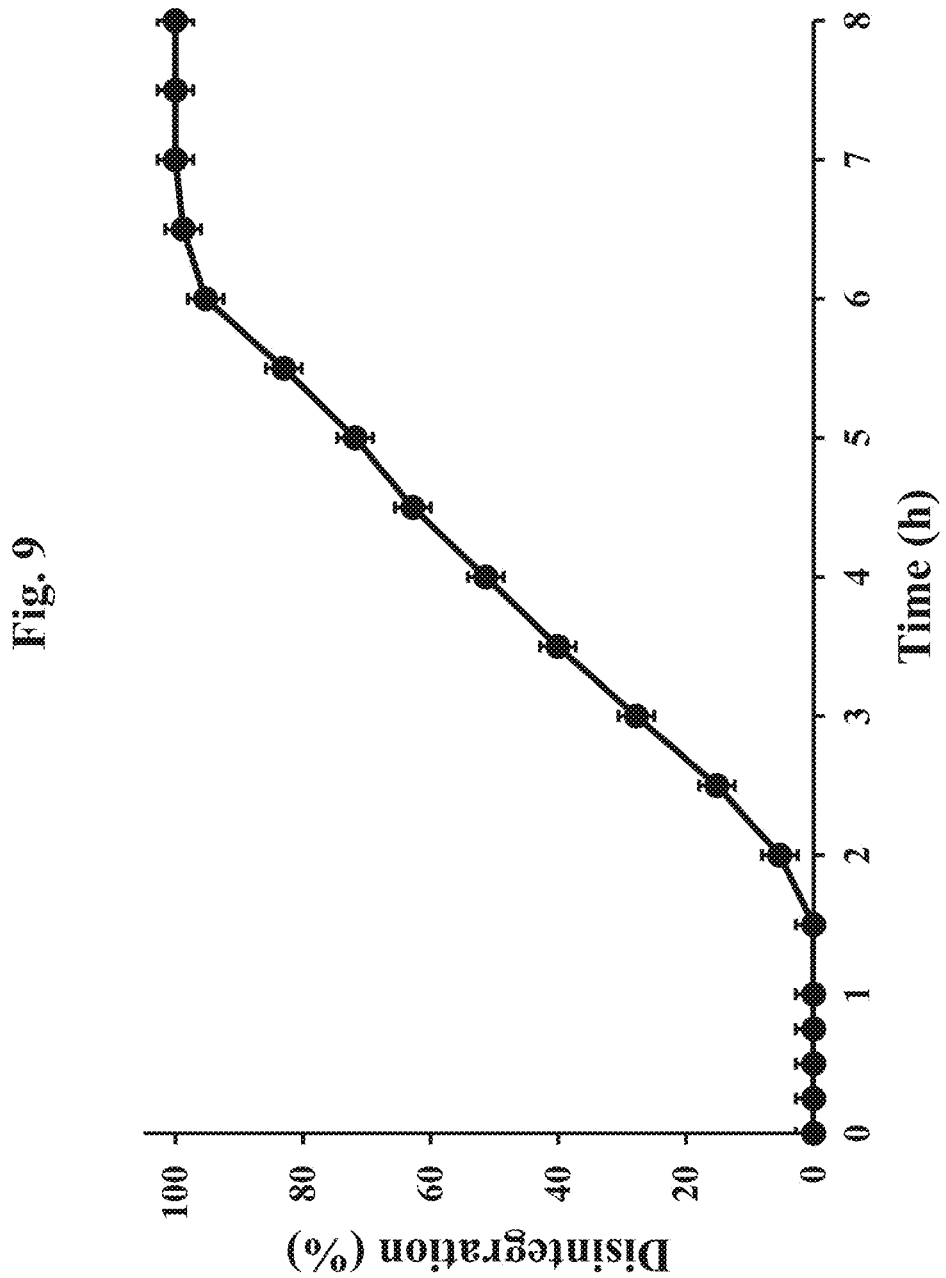
FIG. 9: Disintegration kinetic of the formulation described in Table 13.

Post-gastric survival of probiotics strains and survival of the strains using the formulation described in Table 13 and FIG. 8A, and survival of the unformulated strains are shown in FIG. 8B. The probiotics used were a mixture of *Lactobacillus paracasei, Lactobacillus rhamnosus* and *Lactobacillus plantarum*. Protein:polysaccharide mixtures were at a weight ratio of 90:10. Disintegration kinetics of the formulation described in Table 13 is shown in FIG. 9.

TABLE 13

Three probiotic strains formulation

| | Ingredient | Quantity (mg) |
|---|---|---|
| Protein/polysaccharide powder mixture | Denatured pea proteins-carrageenan | 165 |
| Active ingredient | Probiotics | 110 |
| Additives | MCC | 115 |
| | Magnesium stearate | 6 |
| | Silicon dioxide | 6 |
| | Stearic acid | 50 |

Example 10

Curcumin Tablet Formulation and Release

Figure 10:
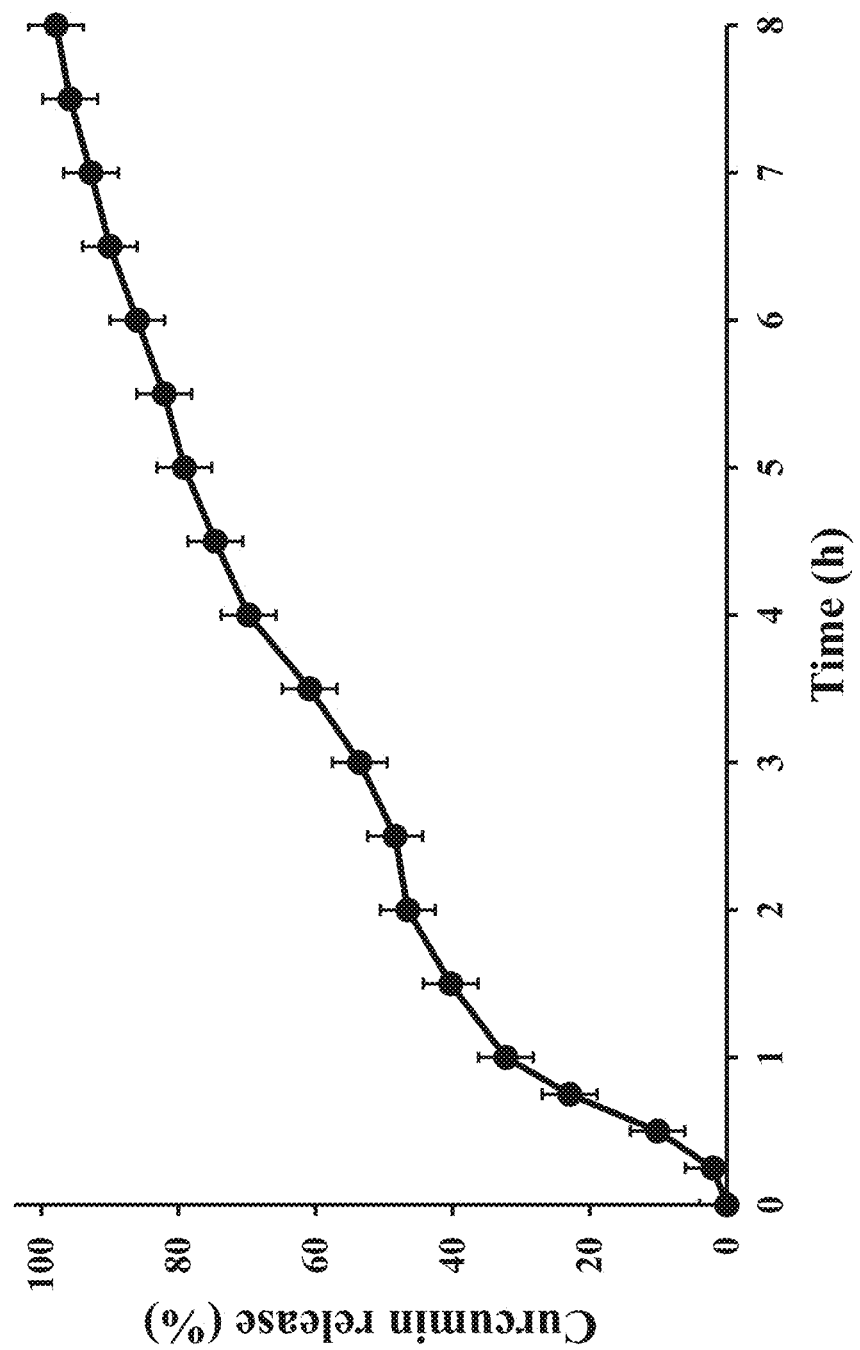
FIG. 10: Dissolution profile obtained from the formulation described in Table 14.

Dissolution profile obtained from the formulation described in Table 14 is shown in FIG. 10. Protein:polysaccharide mixtures were at a ratio of 92:8.

TABLE 14

Curcumin tablet formulation

| | Ingredient | Quantity (mg) |
|---|---|---|
| Protein/polysaccharide powder mixture | Denatured soy proteins-carrageenans | 83 |
| Active ingredient | Curcumin | 225 |
| Additives | MCC | 142 |
| | Magnesium stearate | 4 |
| | Silicon dioxide | 2 |

Example 11

5-HTP Tablet Formulation and Release

Figure 11:
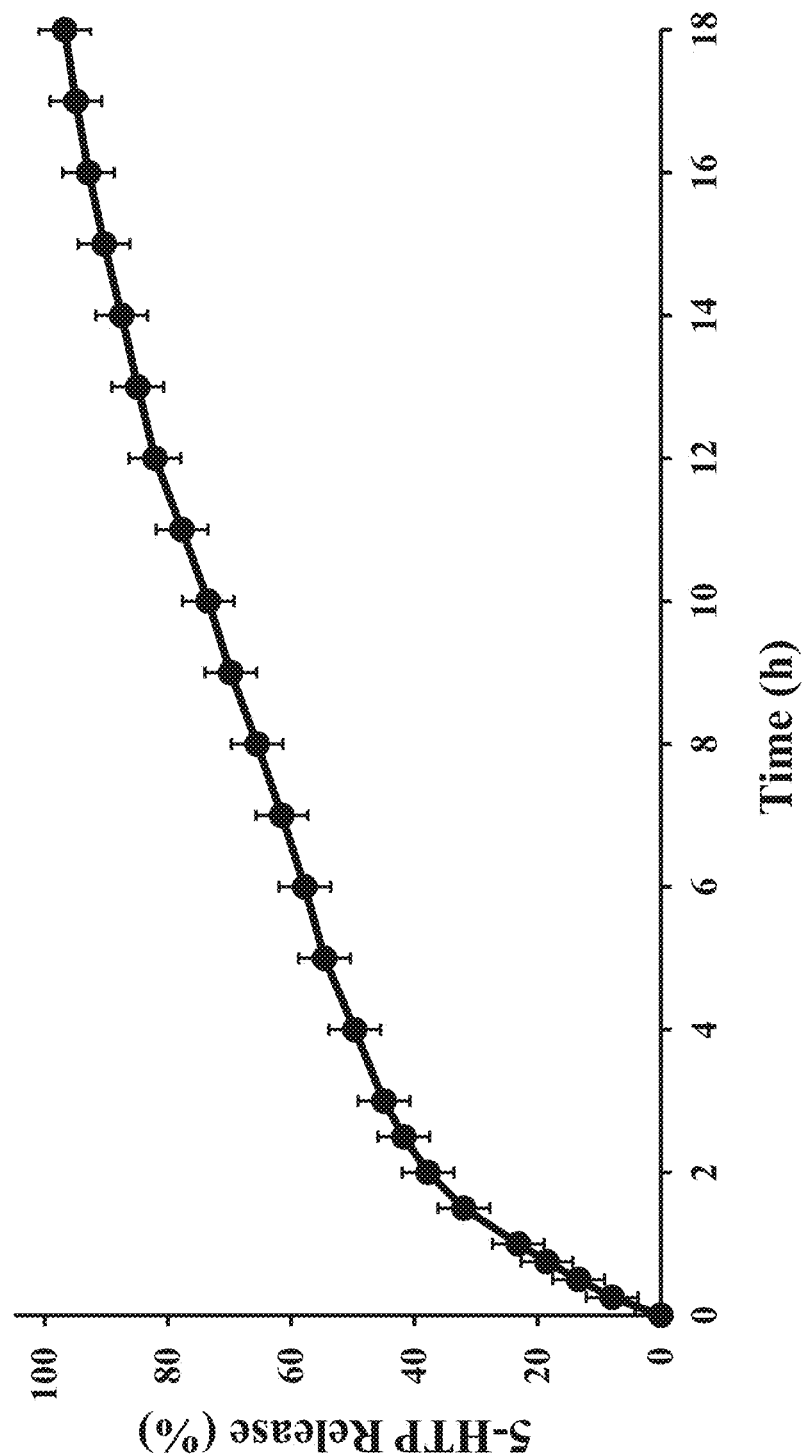
FIG. 11: Dissolution profile obtained from the formulation described in Table 15.

Dissolution profile obtained from the formulation described in Table 15 is shown in FIG. 11. Protein:polysaccharide mixtures were at a ratio of 85:15.

TABLE 15

5-HTP tablet formulation

| | Ingredient | Quantity (mg) |
|---|---|---|
| Protein/polysaccharide powder mixture | Denatured pea proteins-xanthan | 200 |
| Active ingredient | 5-HTP | 100 |
| Additives | MCC and Dibasic Calcium Phosphate | 142 |
| | Magnesium stearate | 6 |
| | Silicon dioxide | 3 |

Example 12

Peppermint Extract Tablet Formulation and Release

Figure 12:
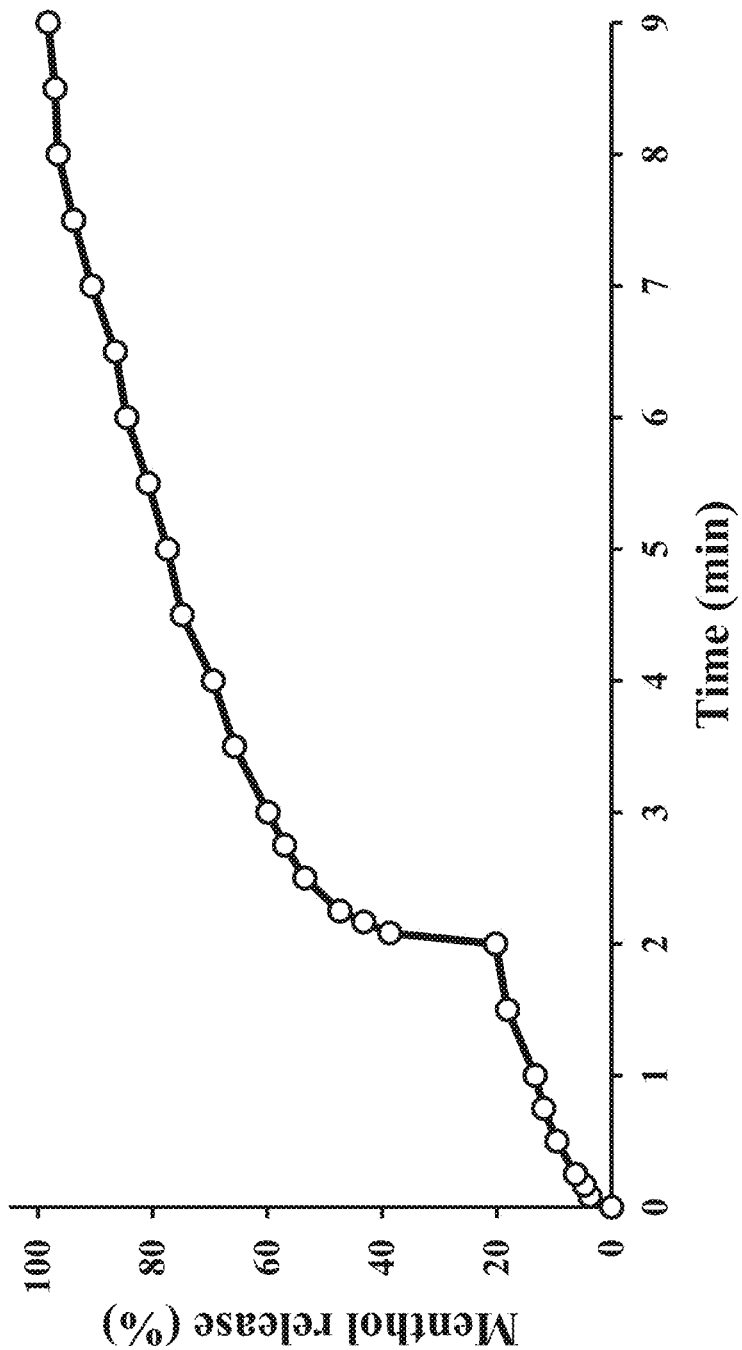
FIG. 12: Dissolution properties of the formulation described in Table 16.

Dissolution properties of the formulation described in Table 16 is shown in FIG. 12. Protein:polysaccharide mixtures were at a ratio of 70:30.

TABLE 16

Peppermint extract tablet formulation

| | Ingredient | Quantity (mg) |
|---|---|---|
| Protein/polysaccharide powder mixture | Succinylated pea proteins-alginate | 72 |
| Active ingredient | Peppermint extract | 250 |
| Additives | MCC | 142 |
| | Stearic acid | 26 |
| | Vitamin B6 | 2 |
| | Magnesium stearate | 6 |
| | Silicon dioxide | 3 |

Example 13

Caffeine Tablet Formulation and Release

Figure 13:
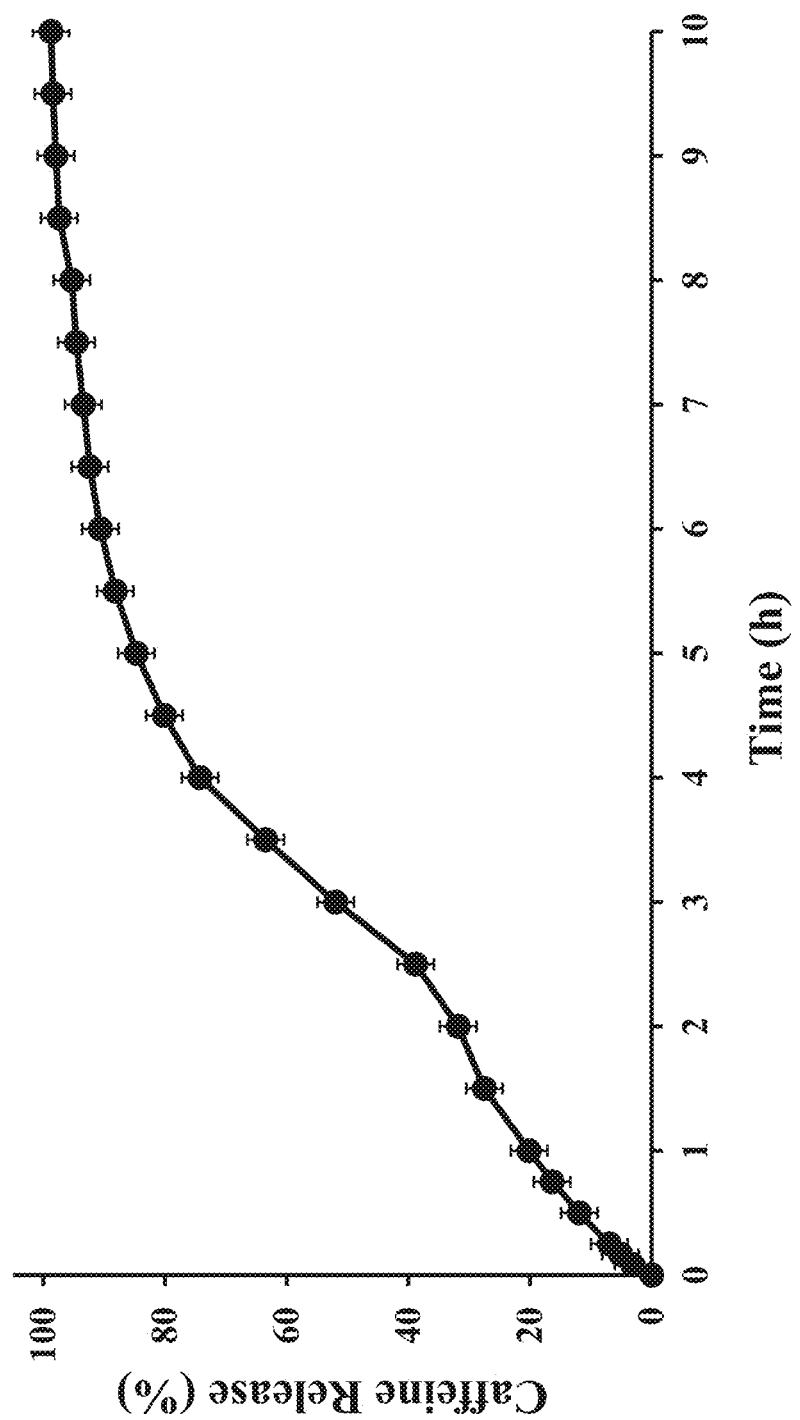
FIG. 13: Dissolution properties of the formulation described in Table 17.

Dissolution properties of the formulation described in Table 17 is shown in FIG. 13. Protein:polysaccharide mixtures were at a ratio of 92:8.

TABLE 17

Caffeine tablet formulation

| | Ingredient | Quantity (mg) |
|---|---|---|
| Protein/polysaccharide powder mixture | Denatured soy proteins-carrageenans | 300 |
| Active ingredient | Caffeine | 150 |
| Additives | MCC | 206 |
| | Magnesium stearate | 8 |
| | Silicon dioxide | 4.5 |

Example 14

Goldenrod Extract/Ginger Tablet Formulation and Release

Figure 14:
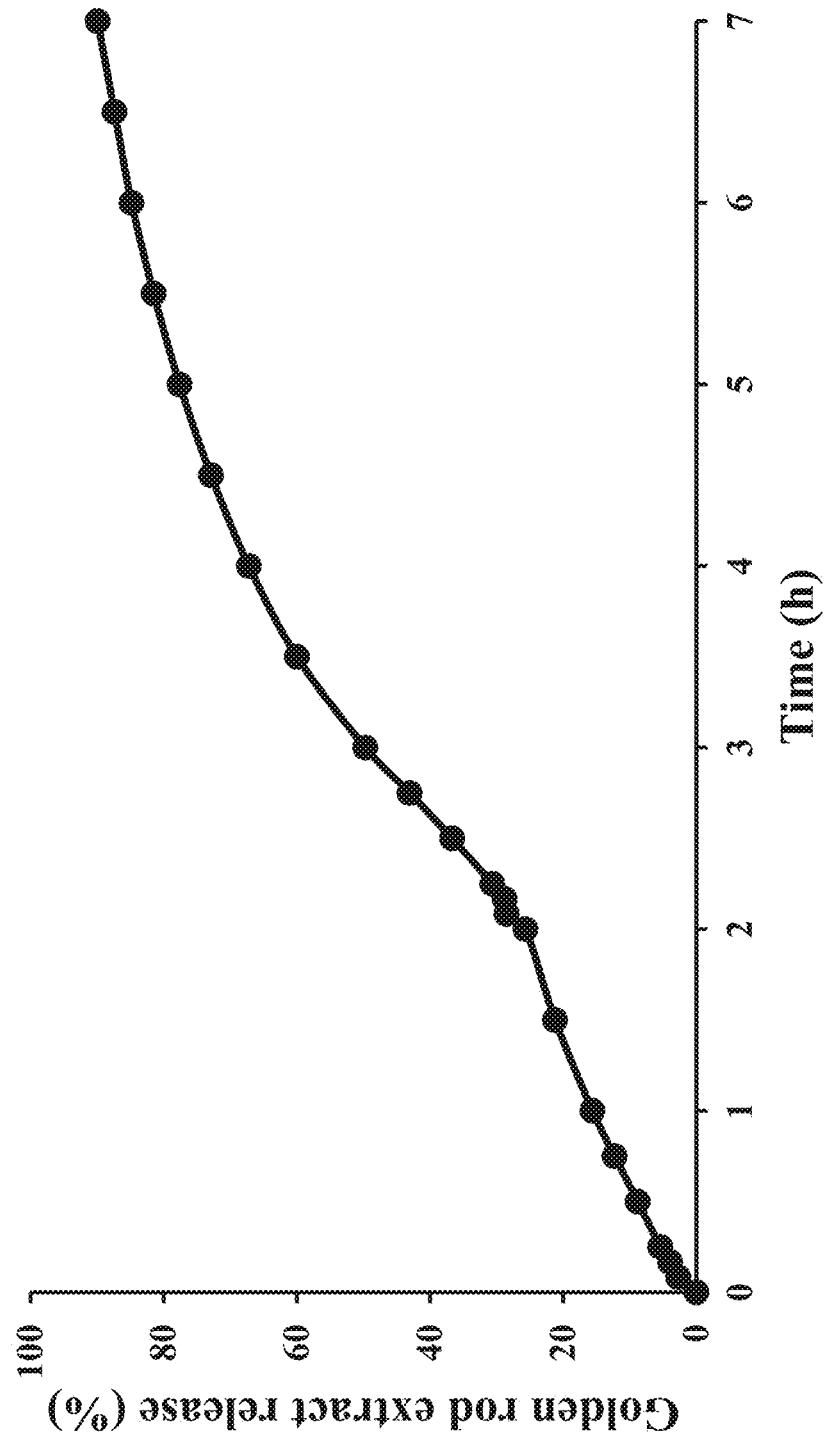
FIG. 14: Dissolution properties of the formulation described in Table 18.

Dissolution properties of the formulation described in Table 18 is shown in FIG. 14. Protein:polysaccharide mixtures were at a ratio of 75:25.

TABLE 18

Goldenrod & ginger tablet formulation

| | Ingredient | Quantity (mg) |
|---|---|---|
| Protein/polysaccharide powder mixture | Native pea proteins-carrageenans | 230 |
| Active ingredients | Goldenrod extract & ginger | 200 |
| | Caffeine | 43 |
| Additives | MCC | 110 |
| | Magnesium stearate | 10 |
| | Silicon dioxide | 9 |

Example 15

*S. boulardii* Tablet Formulation and Release

Figure 15B:
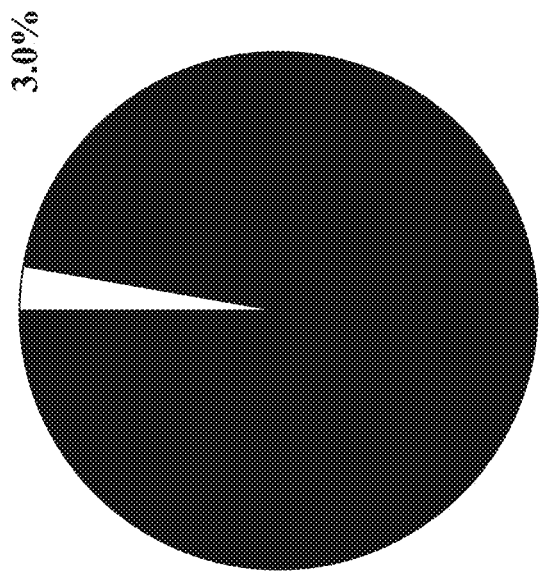
FIG. 15B: Survival of the strain alone (unformulated).
Figure 15A:
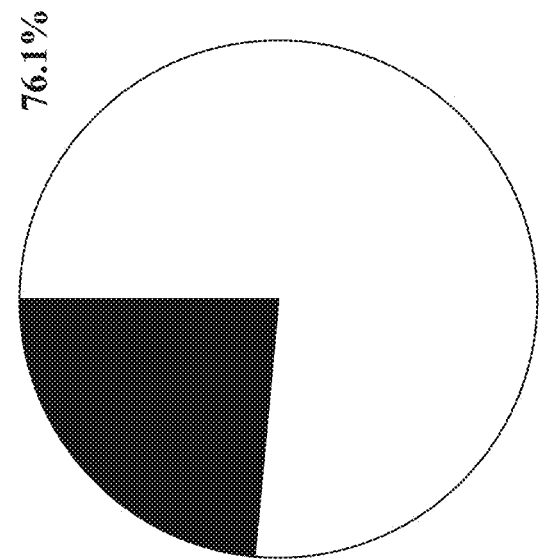
FIG. 15A: Post-gastric survival of *Saccharomyces boulardii*. Survival of the strain using the formulation described in Table 19.
Figure 16:
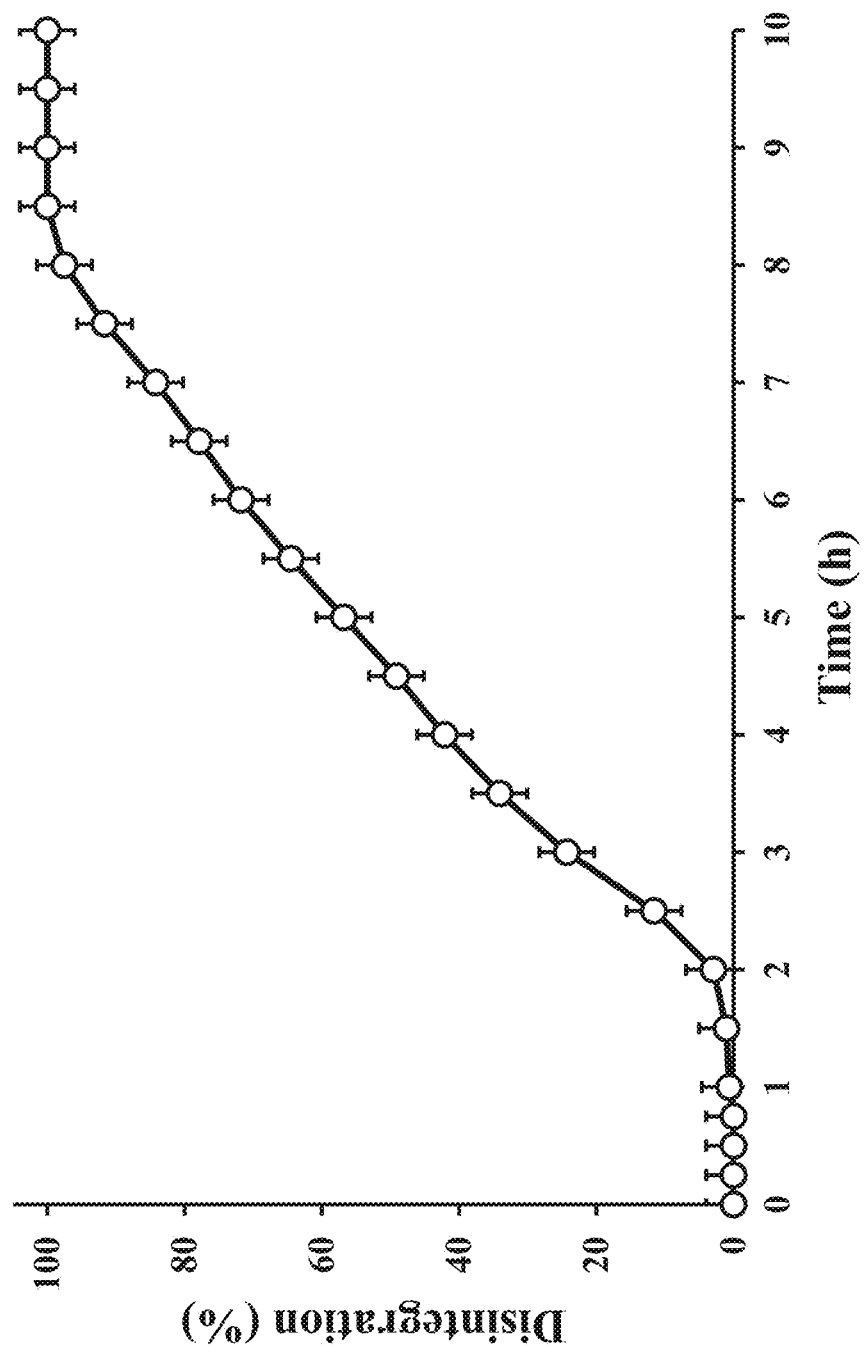
FIG. 16: Disintegration kinetic of the formulation described in Table 19.

Post-gastric survival of *Saccharomyces boulardii*. Survival of the strain using the formulation described in Table 19 is shown in FIG. 15A (76.1%) and survival of the unformulated strain is shown in FIG. 15B (3%). Disintegration kinetic of the formulation described in Table 19 is shown in FIG. 16. Protein:polysaccharide mixtures were at a ratio of 85:15.

TABLE 19

*S. boulardii* tablet formulation

| | Ingredient | Quantity (mg) |
|---|---|---|
| Protein/polysaccharide powder mixture | Succinylated soy proteins-pectin | 180 |
| Active ingredient | *S. boulardii* | 120 |
| Additives | MCC | 126 |
| | Magnesium stearate | 6 |
| | Silicon dioxide | 6 |
| | Stearic acid | 55 |

Example 16

Beta-Alanine Tablet Formulation and Release

Figure 17:
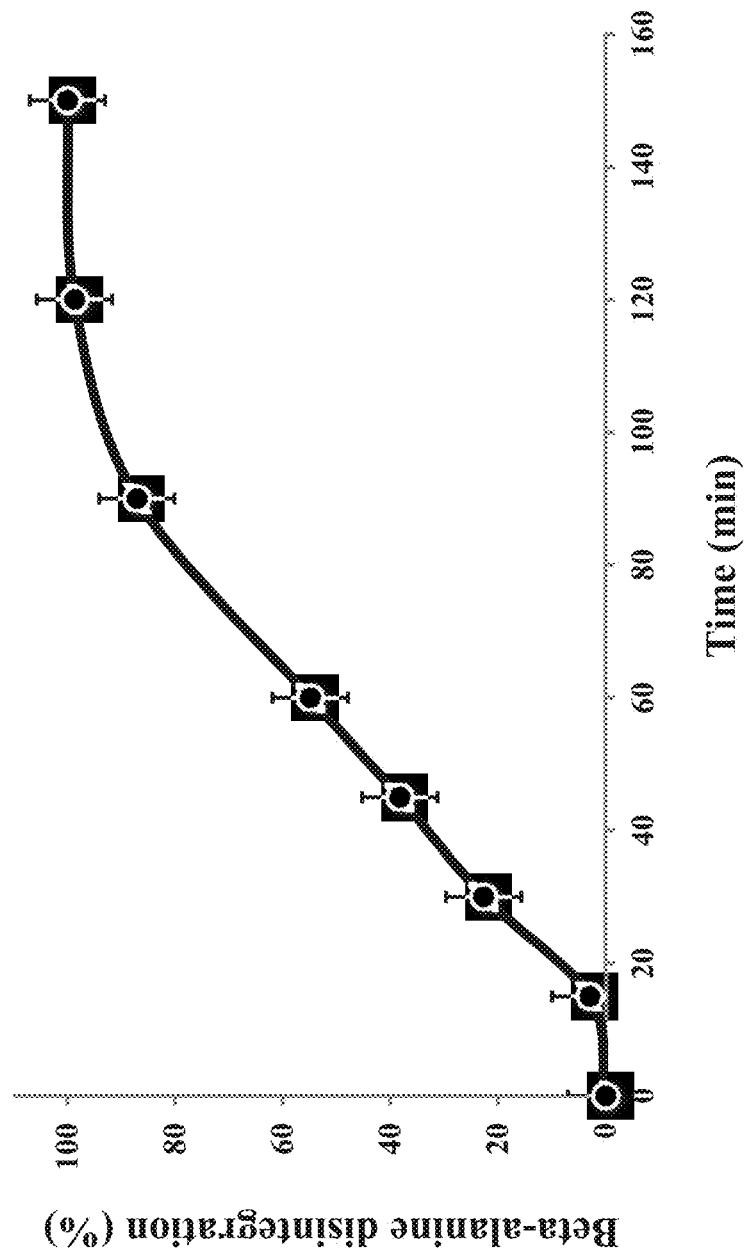
FIG. 17: Dissolution properties of the formulation described in Table 20.

The disintegration kinetics of the formulation described in Table 20 is shown in FIG. 17. Protein:polysaccharide mixtures were at a ratio of 85:15.

TABLE 20

Beta-alanine tablet formulation

| | Ingredient | Quantity (mg) |
|---|---|---|
| Protein/polysaccharide powder mixture | Native pea protein-xanthan | 300 |
| Active ingredient | Beta-alanine | 400 |
| Additives | Nu rice | 25 |
| | Nu flow | 25 |

TABLE 20-continued

Beta-alanine tablet formulation

| | Ingredient | Quantity (mg) |
|---|---|---|
| | Calcium carbonate | 200 |
| | Dextrose | 200 |

Example 17

Peppermint-Vitamin B6 Capsule Formulation and Release

Figure 18:
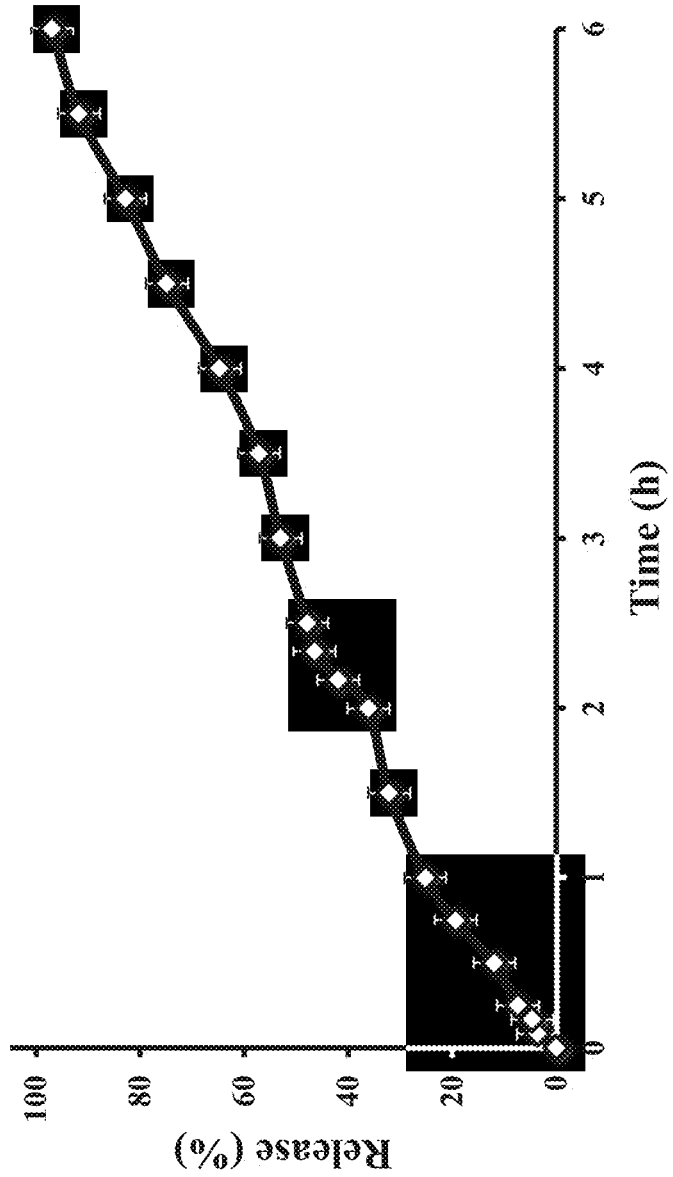
FIG. 18: Dissolution properties of the formulation described in Table 21.

Dissolution properties of the formulation described in Table 21 is shown in FIG. 18 Protein:xanthan:polysaccharide mixtures were at a ratio of 80:10:10.

TABLE 21

Peppermint capsule formulation

| | Ingredient | Quantity (mg) |
|---|---|---|
| Protein/polysaccharide powder mixture | Native pea protein-xanthan-carrageenan | 133 |
| Active ingredient | L-Menthol | 42 |
| Additives | MCC | 150 |
| | Stearic acid | 15 |

Example 18

Melatonin-Ginger Tablet Formulation and Release

Figure 19:
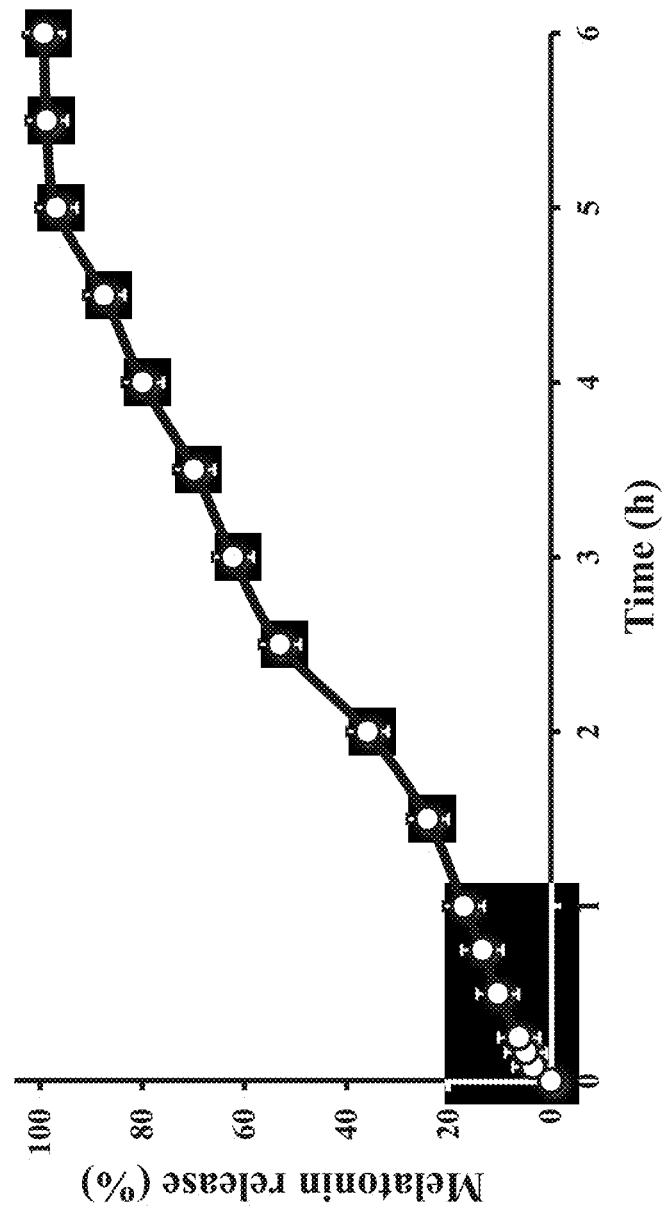
FIG. 19: Dissolution properties of the formulation described in Table 22.

Dissolution properties of the formulation described in Table 22 is shown in FIG. 19. Protein:polysaccharide mixtures were at a ratio of 80:20.

TABLE 22

Melatonin-ginger tablet formulation

| | Ingredient | Quantity (mg) |
|---|---|---|
| Protein/polysaccharide powder mixture | Native pea protein-Xanthan | 100 |
| Active ingredients | Ginger-Probiotics (2:1) | 120 |
| | Melatonin | 5 |
| Additives | MCC | 270 |
| | Magnesium stearate | 5 |
| | Silicon dioxide | 2.5 |

Example 19

Nicotinamide MonoNucleotide (NMN) Tablet Formulation and Release

Figure 20:
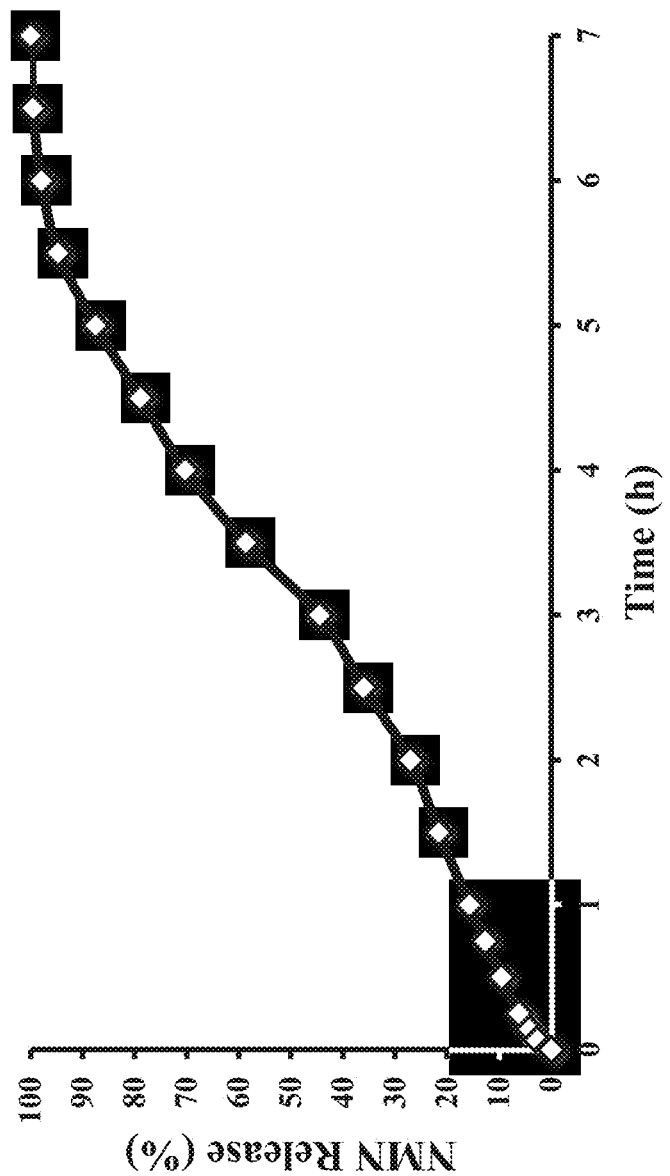
FIG. 20: Dissolution properties of the formulation described in Table 23.

Dissolution properties of the formulation described in Table 23 is shown in FIG. 20. Protein:xanthan:guar gum mixtures were at a ratio of 78:18:4.

TABLE 23

NMN tablet formulation

| | Ingredient | Quantity (mg) |
|---|---|---|
| Protein/polysaccharide powder mixture | Native rice protein-xanthan-guar gum | 300 |

TABLE 23-continued

NMN tablet formulation

| | Ingredient | Quantity (mg) |
|---|---|---|
| Active ingredients | Nicotinamide Mono-Nucleotide (NMN) | 250 |
| Additives | Isomalt | 600 |
| | Stearic acid | 20 |
| | Calcium palmitate | 10 |
| | MCC | 30 |

Example 20

Vitamin C Capsule Formulation and Release

Figure 21:
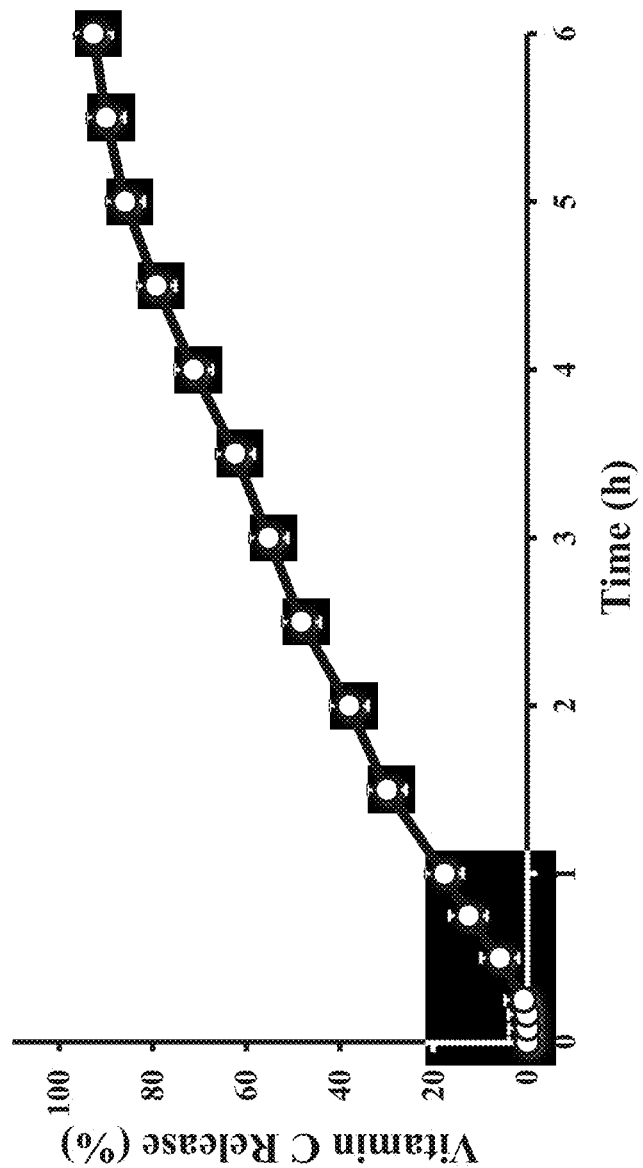
FIG. 21: Dissolution properties of the formulation described in Table 24.

Dissolution properties of the formulation described in Table 24 is shown in FIG. 21. Protein:polysaccharide mixture was at a ratio of 78:22.

TABLE 24

Vitamin C capsule formulation

| | Ingredient | Quantity (mg) |
|---|---|---|
| Protein/polysaccharide powder mixture | Native pea protein-Xanthan | 200 |
| Active ingredients | Vitamin C | 300 |
| Additives | MCC | 120 |
| | Stearic acid | 20 |

Example 21

Pancreatin Tablet Formulation and Release

Figure 22:
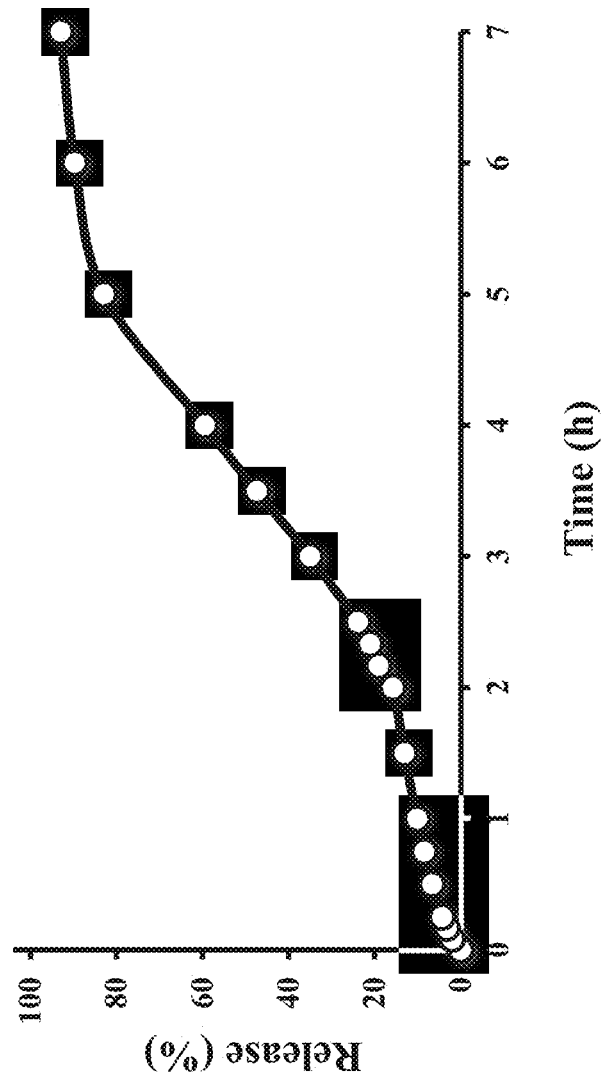
FIG. 22: Dissolution properties of the formulation described in Table 25.
Figure 23:
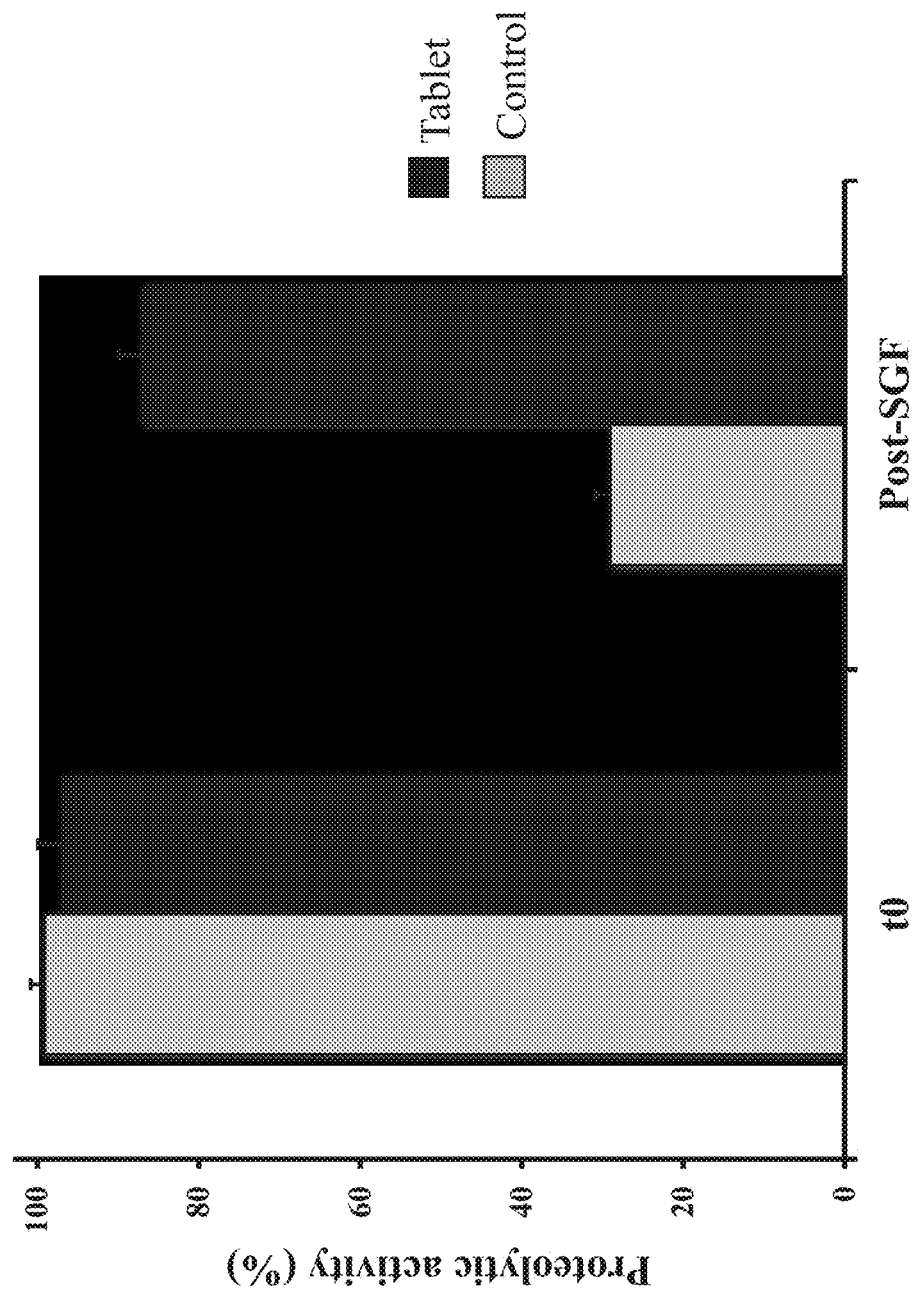
FIG. 23: Post-gastric proteolytic enzyme activity of the formulation described in Table 25.

Dissolution properties of the formulation described in Table 25 are shown in FIG. 22. Protein:xanthan:alginate mixtures were at a ratio of 80:16:4. Post-SGF enzyme proteolytic activity of pancreatin versus negative control is shown in FIG. 23.

TABLE 25

Pancreatin tablet formulation

| | Ingredient | Quantity (mg) |
|---|---|---|
| Protein/polysaccharide powder mixture | Native whey protein-xanthan-alginate | 250 |
| Active ingredients | Pancreatin | 100 |
| Additives | Dicalcium phosphate | 800 |
| | Stearic acid | 30 |
| | Calcium palmitate | 15 |
| | MCC | 30 |

Example 22

Garlic Tablet Formulation and Release

Figure 24:
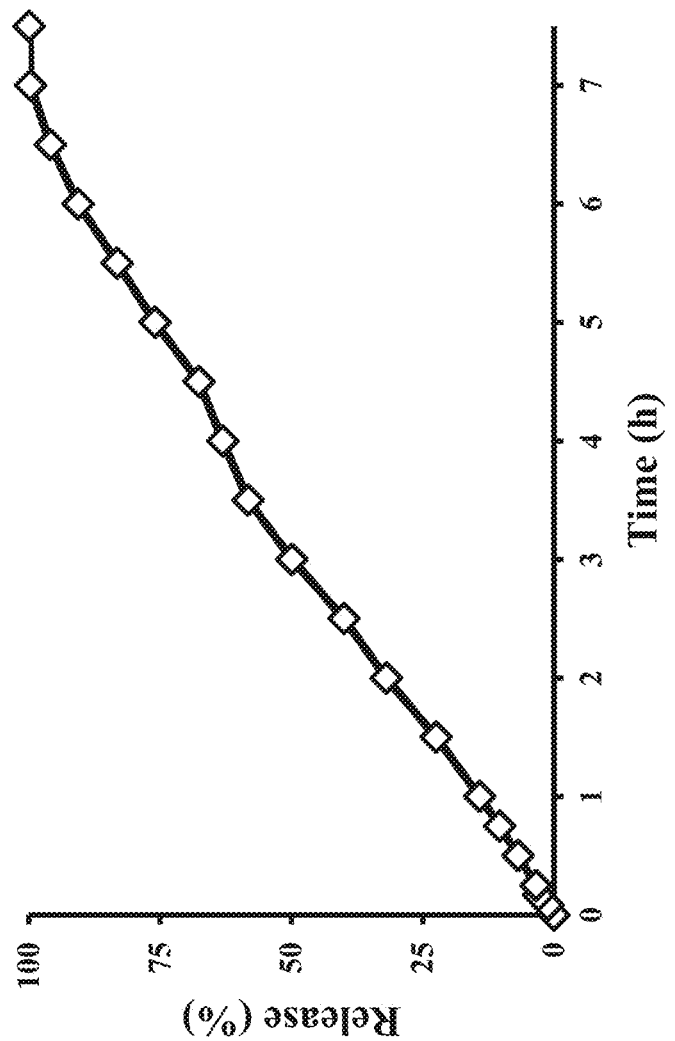
FIG. 24: Dissolution properties of the formulation described in Table 26.

Dissolution properties of the formulation described in Table 26 are shown in FIG. 24. Protein:polysaccharide was at a ratio of 86:14.

TABLE 26

Garlic tablet formulation

| | Ingredient | Quantity (mg) |
|---|---|---|
| Protein/polysaccharide powder mixture | Denatured pea protein-xanthan | 200 |
| Active ingredients | Garlic extract | 400 |
| Additives | Dicalcium phosphate | 260 |
| | Stearic acid | 30 |
| | Calcium palmitate | 15 |
| | Silicon dioxide | 5 |
| | MCC | 100 |

REFERENCES

Beakawi Al-Hashemi, H. M., Baghabra Al-Amoudi, O. S. (2018). A review on the angle of repose of granular materials. Powder technology, 330, 397-417.

Boschini, F., Delaval, V., Traina, K., Vandewalle, N., Lumay, G. (2015). Linking flowability and granulometry of lactose powders. International Journal of Pharmaceutics, 494, 312-320.

Carr, R. L., (1965) Evaluating Flow Properties of Solids. Chem. Eng. 72, 163-168.

de Kruif, C. G., Weinbreck, F., de Vries, R. (2004). Complex coacervation of proteins and anionic polysaccharides. Current opinion in colloid and interface science, 9, 340-349.

Gilbert, V., Rouabhia, M., Wang, H., Arnould, A-L., Remondetto, G. & Subirade, M. (2005). Characterization and evaluation of whey proteins-based films as substrates for in vitro cell cultures. Biomaterials, 26, 7471-7480.

Schmitt, C. (2000). Étude de la coacervation complexe entre la β-lactoglobuline et la gomme d'acacia en solution aqueuse. Theses INSAIA, France. 217 pp.

Syrbe, A., Bauer, W. J. & Klostermeyer, H. (1998). Polymer science concepts in dairy systems-An overview of milk protein and food hydrocolloid interaction. International Dairy Journal, 8, 179-193.

Tolstoguzov, V. B. (1997). Protein-polysaccharide interactions. In: S. Damodaran & A. Paraf, Food Proteins and their Applications (pp 171-198). New York: Marcel Dekker.

The invention claimed is:

1. An oral delivery system consisting essentially of a dry active ingredient dispersed in a dry homogenous mixture of blended protein and polysaccharide powders as coacervate-forming agents, wherein:
   (i) the dry homogenous mixture of blended protein and polysaccharide powders is uncoacervated;
   (ii) the polysaccharide powder, prior to blending, has a Carr compressibility index of greater than 25%; and
   (iii) in the dry homogenous mixture of blended coacervate-forming agents, the amount by weight of protein powder is greater than the amount by weight of the polysaccharide powder, thereby enabling the protein and polysaccharide powders to form a protein/polysaccharide complex coacervate in situ upon immersion of the oral delivery system in a gastric fluid, thereby conferring gastric protection and/or modified release to the active ingredient.

2. The oral delivery system of claim 1, wherein the active ingredient is a dietary supplement.

3. The oral delivery system of claim 1, further comprising one or more nutraceutically or pharmaceutically acceptable excipients and/or additives.

4. The oral delivery system of claim 3, wherein the additive comprises microcrystalline cellulose, magnesium stearate, and/or silicon dioxide.

5. The oral delivery system of claim 1, which is a tablet or a capsule.

6. The oral delivery system of claim 1, wherein the oral delivery system does not comprise an enteric coating.

7. The oral delivery system of claim 1, wherein the polysaccharide powder has a Carr compressibility index greater than 27%.

8. The oral delivery system of claim 1, wherein the polysaccharide powder has a Carr compressibility index greater than 30%.

9. The oral delivery system of claim 1, wherein the polysaccharide powder has a Carr compressibility index greater than 35%.

10. The oral delivery system of claim 1, wherein the weight ratio of polysaccharide powder to protein powder in the oral delivery system is 1:20 to 1:2.

11. The oral delivery system of claim 1, wherein the oral delivery system comprises 5% to 50% w/w of the protein and polysaccharide mixture.

12. The oral delivery system of claim 1, wherein the protein powder comprises native proteins.

13. The oral delivery system of claim 1, wherein the protein powder comprises denatured proteins.

14. The oral delivery system of claim 1, wherein the protein powder comprises chemically unmodified proteins.

15. The oral delivery system of claim 1, wherein the protein powder comprises chemically modified proteins.

16. The oral delivery system of claim 1, wherein the polysaccharide powder comprises chemically unmodified polysaccharides.

17. The oral delivery system of claim 1, wherein the polysaccharide powder comprises chemically modified polysaccharides.

18. The oral delivery system of claim 1, wherein the polysaccharide powder comprises carrageenan, xanthan gum, alginate, pectin, agar, gellan, guar gum, carboxymethylcellulose, locust bean gum, mannan, glucomannan, hyaluronan, tamarind gum, *psyllium* seed gum, tara gum, acacia gum, arabic gum, ghatti gum, tragacanth gum, karaya gum, *cassia* gum, rhamsan gum, welan gum, macrophomopsis gum, curdlan, pullulan, fucoidan, or any mixture thereof.

19. The oral delivery system of claim 1, wherein the active ingredient is a drug.

20. The oral delivery system of claim 1, wherein the active ingredient is a probiotic or herbal supplement.

21. The oral delivery system of claim 1, wherein the active ingredient is a vitamin or an amino acid.

22. The oral delivery system of claim 1, wherein the active ingredient is a food extract.

* * * * *